(12) United States Patent
Bresolin et al.

(10) Patent No.: US 8,595,609 B2
(45) Date of Patent: Nov. 26, 2013

(54) METHODS, SYSTEMS AND COMPUTER PROGRAM PRODUCTS FOR CREATING AND MODIFYING LABELS USED BY PHARMACEUTICAL DISPENSING SYSTEMS

(75) Inventors: Stefano Bresolin, Garner, NC (US); Matthew Johnson, Raleigh, NC (US)

(73) Assignee: Parata Systems, LLC, Durham, NC (US)

( * ) Notice: Subject to any disclaimer, the term of this patent is extended or adjusted under 35 U.S.C. 154(b) by 343 days.

(21) Appl. No.: 12/463,646

(22) Filed: May 11, 2009

(65) Prior Publication Data

US 2009/0287992 A1 Nov. 19, 2009

Related U.S. Application Data

(60) Provisional application No. 61/053,739, filed on May 16, 2008.

(51) Int. Cl.
*G06F 17/00* (2006.01)
*G06F 3/01* (2006.01)
*G06F 3/041* (2006.01)
*G06F 3/048* (2013.01)

(52) U.S. Cl.
USPC .......................... 715/222; 715/226; 715/702

(58) Field of Classification Search
USPC ................................................. 715/222, 769
See application file for complete search history.

(56) References Cited

U.S. PATENT DOCUMENTS

| | | | |
|---|---|---|---|
| 2,002,753 A | 5/1935 | Parks et al. | |
| 2,442,025 A | 5/1948 | Smith | |
| 3,194,431 A | 7/1965 | Garvin | |
| 3,938,700 A | 2/1976 | Camp et al. | |
| 4,232,800 A | 11/1980 | Martin et al. | |
| 4,303,179 A | 12/1981 | Spring | |
| 4,546,901 A | 10/1985 | Buttarazzi | |
| 4,694,230 A | 9/1987 | Slocum et al. | |
| 4,740,025 A | 4/1988 | Nelson | |
| 4,782,274 A | 11/1988 | Teegarden et al. | |
| 4,812,629 A | 3/1989 | O'Neil et al. | |
| 5,337,919 A | 8/1994 | Spaulding et al. | |
| 5,720,154 A | 2/1998 | Lasher et al. | |
| 5,771,657 A | 6/1998 | Lasher et al. | |
| 5,907,493 A | 5/1999 | Boyer et al. | |
| 6,202,923 B1 | 3/2001 | Boyer et al. | |
| 6,370,841 B1 | 4/2002 | Chudy et al. | |
| RE37,829 E | 9/2002 | Charhut et al. | |
| 6,742,671 B2 | 6/2004 | Hebron et al. | |
| 7,096,212 B2 | 8/2006 | Tribble et al. | |
| 7,228,198 B2 | 6/2007 | Vollm et al. | |
| 7,650,732 B2 | 1/2010 | Pearson et al. | |
| 2003/0236715 A1* | 12/2003 | Leo ................................ 705/26 |
| 2004/0133705 A1 | 7/2004 | Broussard et al. | |
| 2007/0096945 A1* | 5/2007 | Rasmussen et al. ....... 340/995.1 |
| 2007/0293982 A1* | 12/2007 | Rosenblum .................. 700/235 |

* cited by examiner

*Primary Examiner* — Doug Hutton, Jr.
*Assistant Examiner* — Ariel Mercado
(74) *Attorney, Agent, or Firm* — Myers Bigel Sibley & Sajovec, P.A.

(57) ABSTRACT

Apparatus, methods and computer program products for creating and modifying labels for use by pharmaceutical dispensing machines are provided. A pharmaceutical dispensing apparatus includes a touch screen, a processor, memory coupled to the processor, and a computer program residing in the memory that is executable by the processor for guiding a user through a process of designing a label via the touch screen. The computer program displays a label template adapted to receive a plurality of data fields inputted by a user therein, wherein each data field is adapted to receive and display respective data. The computer program includes a label wizard that guides a user through the process of designing a label within the label template.

17 Claims, 28 Drawing Sheets

| Field | Component | Definition |
|---|---|---|
| VialNum | Text | The number of the vial, of multiple vials are required to fill a single order. |
| TotalVials | Text | Total number of vials in a single order |
| Parata Barcode | Text | |
| LotNum | Text | Lot number of the drug |
| FillDate | Various date formats | Date the order is filled |
| ExpDate | Various date formats | Date the drug expires |
| FillQuantity | Text | Quantity actually contained in the vial. |
| HostScanCode | Text | |
| RxOrderNum | Text | Prescription order number |
| PatientName | Various name fields | Patient name |
| DrugNDC | Text | NDC number specific to the drug. |
| DrugName | Text | |
| Quantity | Text | |
| PromisedDate | Various date formats | The date the pharmacy has told the patient the order will be ready. |
| PRN | Text | |

FIG. 5

| Data Field | Definition | Components |
|---|---|---|
| ExpDate | Date after which drug is no longer useable | Date formats |
| DatePrinted | Date the label is physically printed | Date formats |
| DrugName | | Text |
| DrugNDC | NDC number associated with the particular medication | Text |
| RPH | | Text |
| LotNr | | Text |
| MaxCapacity | | Text |

FIG. 8A

| Logic Procedures | Definition |
|---|---|
| Boolean GTE(String str1, String str2) | String 1 greater than or equal to string 2 |
| Boolean GT(String str1, String str2) | String 1 greater than string 2 |
| Boolean LTE(String str1, String str2) | String 1 less than or equal to string 2 |
| Boolean LT(String str1, String str2) | String 1 less than string 2 |
| Boolean EQ(String str1, String str2) | String 1 equal to string 2 |
| Boolean AND(Boolean op1, Boolean op2) | Both op1 and op2 are true |
| Boolean OR(Boolean op1, Boolean op2) | Either op1 and op2 are true |
| Boolean NOT(Boolean op) | Op is not true |
| Boolean ISNOTEMPTY(String Expression) | String expression contains any characters. |

FIG. 8B

| Text Procedures | Definition |
|---|---|
| String DROPLEADZERO(String str) | Truncates strings with a leading zero |
| String MASKUPTO(String text, Int32 nonMaskedLength) | Reveals the designated number of characters (the rest are blocked out) |
| String LEFT(String str, Int32 len) | Removes the designated number of characters starting from the left of the string. |
| String SUBString(String str, Int32 start, Int32 len) | Selects a substring of length LEN, beginning at character position START. i.e. SUBSTRING(Megan,3,3)=gan |
| String REMNL(String str) | Remove carriage returns from end of string |
| String IFTHEN(Boolean condition, String Expression) | If condition is met, execute specified string. |
| String IFTHENELSE(Boolean condition, String expression1, String expression2 | If condition is met, execute expression 1. Otherwise, execute expression 2. |

FIG. 8C

| Other Procedures | Definition |
|---|---|
| Int32 NUM(String str) | Returns the numeric value of the string. |
| Int32 LEN(String str) | Returns the number of characters in the string. |

FIG. 8D

METHODS, SYSTEMS AND COMPUTER PROGRAM PRODUCTS FOR CREATING AND MODIFYING LABELS USED BY PHARMACEUTICAL DISPENSING SYSTEMS

RELATED APPLICATION

This application claims the benefit of and priority to U.S. Provisional Patent Application No. 61/053,739, filed May 16, 2008, the disclosure of which is incorporated herein by reference as if set forth in its entirety.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to the dispensing of prescriptions of pharmaceuticals and, more particularly, to automated dispensing of pharmaceuticals.

BACKGROUND

Pharmacy generally began with the compounding of medicines, which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable. Various attempts have been made to automate the pharmacy environment. Different exemplary approaches are shown in U.S. Pat. No. 5,337,919 to Spaulding et al. and U.S. Pat. Nos. 6,006,946; 6,036,812 and 6,176,392 to Williams et al. As automated pharmacy machines have become substantially more robust and complex, operating software that is correspondingly robust is needed to facilitate user interaction and control of these machines.

SUMMARY

In view of the above discussion, apparatus, methods and computer program products for creating and modifying labels for use by pharmaceutical dispensing machines are provided. According to some embodiments of the present invention, a pharmaceutical dispensing apparatus includes a touch screen, a processor, memory coupled to the processor, and a computer program residing in the memory that is executable by the processor for guiding a user through a process of designing a label via the touch screen. The pharmaceutical dispensing apparatus then uses the designed label to produce actual labels for attachment to pill containers during prescription fulfillment operations.

The computer program displays a label template adapted to receive a plurality of data fields inputted by a user therein, wherein each data field is adapted to receive and display respective data. Some of the data fields displayed within the label template may automatically receive and display information from data storage in response to display thereof within the label template. The computer program includes a label wizard that guides a user through the process of creating a label within the label template. The label wizard sequentially displays a plurality of GUIs within the touch screen that guide the user through a process of adding data fields to the label template and entering data within the data fields.

Each data field within the label template can be moved around within the label template by a user's finger or stylus in contact with the touch screen. In addition, a plurality of touch-activated GUI controls are displayed adjacent to the label template. The GUI controls allow a user to perform one or more of the following functions: change data field size, change data field orientation, and change font type and size of alphanumeric characters displayed within a data field. In addition, a touch-activated GUI control (e.g., a slider control, etc.) is displayed adjacent to the template that allows a user to zoom the display of a data field in the template. A touch-activated GUI control is displayed adjacent to the template that allows a user to zoom the display of the template within the touch screen.

According to other embodiments of the present invention a pharmaceutical dispensing apparatus includes a touch screen, a processor, memory coupled to the processor, a computer program residing in the memory that is executable by the processor, a label printer that prints prescription labels for pharmaceutical vials, and a labeling station that applies printed labels to pharmaceutical vials, wherein the labeling station is positioned to receive a printed label from the label printer. The computer program includes a label wizard that guides users through a process of creating/modifying a prescription label via the touch screen. The computer program displays a label template adapted to receive a plurality of data fields, wherein each data field is adapted to receive and display respective data, and wherein the label wizard sequentially displays a plurality of GUIs within the touch screen that guide the user through a process of adding data fields to the label template and entering data within the data fields. Each data field can be moved around within the label template by a user's finger or stylus in contact with the touch screen.

According to some embodiments of the present invention, an apparatus includes a touch screen, a processor, memory coupled to the processor, and a computer program residing in the memory that is executable by the processor for guiding a user through a process of designing/modifying a prescription label via the touch screen. The computer program displays a label template adapted to receive a plurality of data fields inputted by a user therein, wherein each data field is adapted to receive and display respective prescription data. The computer program displays a label template adapted to receive a plurality of data fields inputted by a user therein, wherein each data field is adapted to receive and display respective data. Some of the data fields displayed within the label template may automatically receive and display information from data storage in response to display thereof within the label template. The computer program includes a label wizard that guides a user through the process of creating/modifying a label within the label template. The label wizard sequentially displays a plurality of GUIs within the touch screen that guide the user through a process of adding data fields to the label template and entering data within the data fields.

Each data field within the label template can be moved around within the label template by a user's finger or stylus in contact with the touch screen. In addition, a plurality of touch-activated GUI controls are displayed adjacent to the label template. The GUI controls allow a user to perform one or more of the following functions: change data field size, change data field orientation, and change font type and size of alphanumeric characters displayed within a data field.

According to some embodiments of the present invention, a method of creating/modifying a prescription label for a pharmaceutical vial includes displaying a data field within a label template on a touch screen, wherein the data field is movably positionable within the label template by a user's finger or stylus in contact with the touch screen, and sequentially displaying a plurality of GUIs within the touch screen, wherein the plurality of GUIs are configured to guide a user through a process of entering data within the data field.

According to some embodiments of the present invention, a method of creating/modifying a label for use by a pharmaceutical dispensing apparatus includes sequentially displaying a plurality of GUIs within a touch screen of the pharmaceutical dispensing apparatus, wherein the plurality of GUIs are configured to guide a user through a process of adding data fields to a label template and entering data within the data fields.

BRIEF DESCRIPTION OF THE DRAWINGS

FIGS. 4-24 are graphical user interfaces (GUIs) produced by a label wizard that allow a user to create and modify labels for use by the automated pharmacy machine of FIGS. 2-3, in accordance with various embodiments of the present invention.

DETAILED DESCRIPTION

Figure 1:
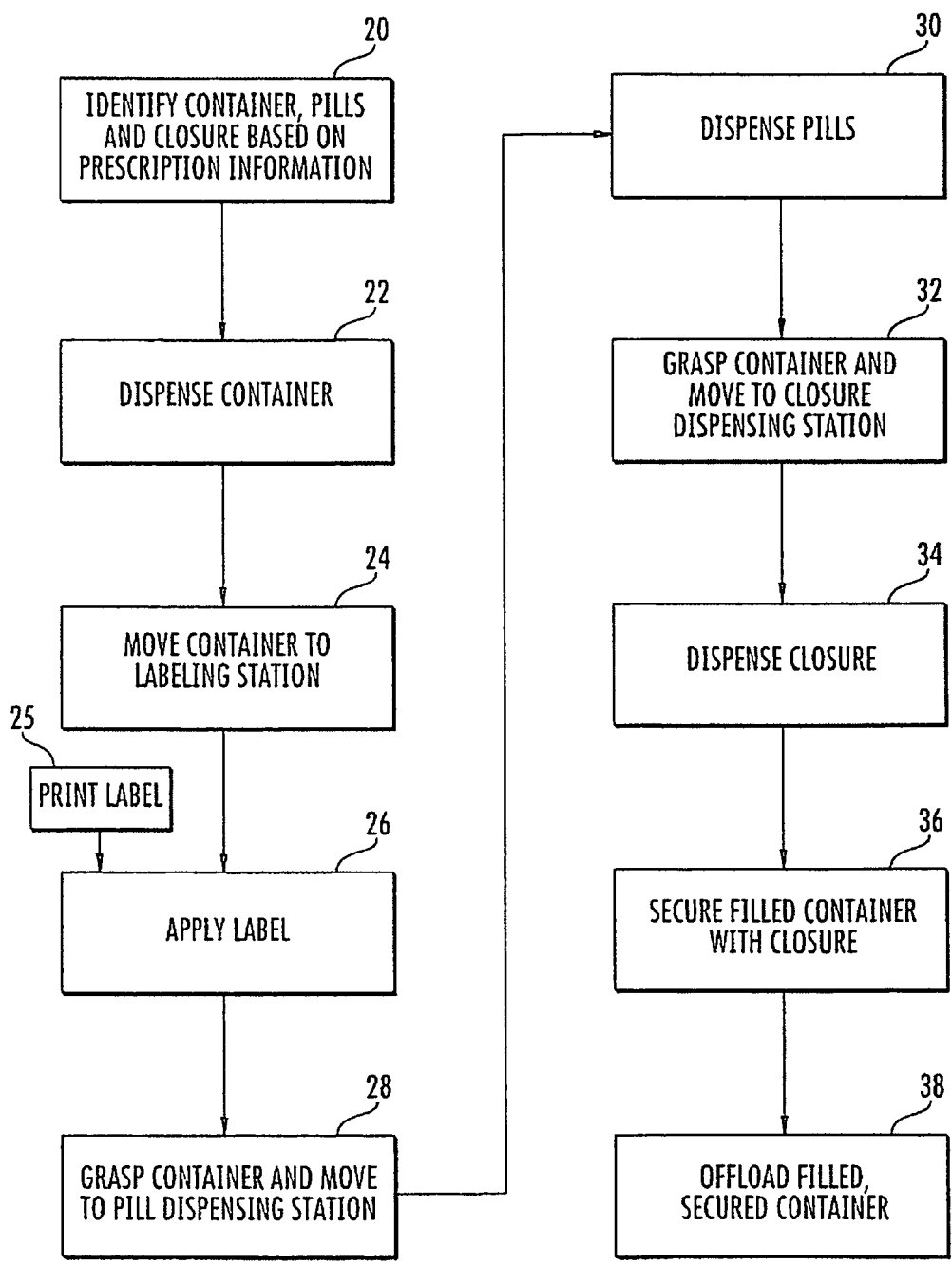
FIG. 1 is a flow chart depicting operations that can be carried out by automated pharmacy machines, according to some embodiments of the present invention.

The present invention now will be described more fully hereinafter with reference to the accompanying drawings, in which illustrated embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first graphical user interface (GUI) could be termed a second GUI, and, similarly, a second GUI could be termed a first GUI without departing from the teachings of the disclosure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "container", as used herein, refers to any type of container including pill containers or vials used to fill a prescription, as well as "stock" bottles that contain pills used to refill cells on the replenishing side of a pharmacy dispensing apparatus.

The term "pills" refers to any type of medicament that can be counted and dispensed by an automated and semi-automated pharmacy machine including, but not limited to, capsules, tablets, caplets, lozenges, and the like.

The term "wizard", as used herein, refers to a computer utility designed to simplify the execution of lengthy or complicated tasks. As known to those of skill in the art, a wizard is essentially a programmatic method of providing guidance to a user via GUIs.

The term "zoom", as used herein, refers to both enlarging and reducing the view of a data field displayed within a label template, and also refers to both enlarging and reducing the view of a displayed label template.

The present invention may be embodied as systems, methods, and/or computer program products for creating and modifying labels for use by an automated pharmacy machine. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

The present invention is described herein with reference to GUIs, flowchart illustrations and block diagram illustrations of methods, systems, and computer program products for creating and modifying labels for use by pharmaceutical dispensing machines, both automated and semi-automated. It will be understood that each block of the flowchart and/or block diagram illustrations, and combinations of blocks in the flowchart and/or block diagram illustrations, may be implemented by computer program instructions and/or hardware operations. These computer program instructions are provided to a processor, or other programmable data processing apparatus to produce a machine, such that the instructions, which execute via the processor and create means for implementing the functions specified in the GUIs, flowcharts and block diagram blocks.

These computer program instructions may also be stored in a computer usable or computer-readable memory such that the instructions produce an article of manufacture including instructions that implement the functions specified in the GUIs, flowcharts and block diagram blocks.

The computer program instructions may also be loaded onto a controller or other programmable data processing apparatus to cause a series of operational steps to be performed on the controller or other programmable apparatus to produce a computer implemented process such that the instructions that execute on the controller or other programmable apparatus provide steps for implementing the functions specified in the GUIs, flowcharts, and block diagram blocks.

Referring to FIG. 1, an exemplary process for filling a prescription order via automated/semi-automated pharmaceutical dispensing apparatus will now be described. The process begins with the identification of the proper container (i.e., a vial that will be used to contain the dispensed medicine), the identification of pills, and the identification of the type of closure to be used on the container based on a patient's prescription order information (Block 20) in a pharmaceutical dispensing apparatus (e.g., automatic pharmaceutical dispensing apparatus 40, FIGS. 2-3). A container of the proper size is dispensed at a container dispensing station (Block 22); the container is then moved to a labeling station (Block 24). A printing station prints a label (Block 25) that is applied to the container at the labeling station (Block 26), after which the labeled container is transferred to a pill dispensing station (Block 28), from which the designated pills are dispensed in the designated amount into the container (Block 30). The filled container is then moved to a closure dispensing station (Block 32), where a closure of the proper size has been dispensed (Block 34). The filled container is secured with a closure (Block 36), then transported to an offload station and offloaded (Block 38).

Figure 2:
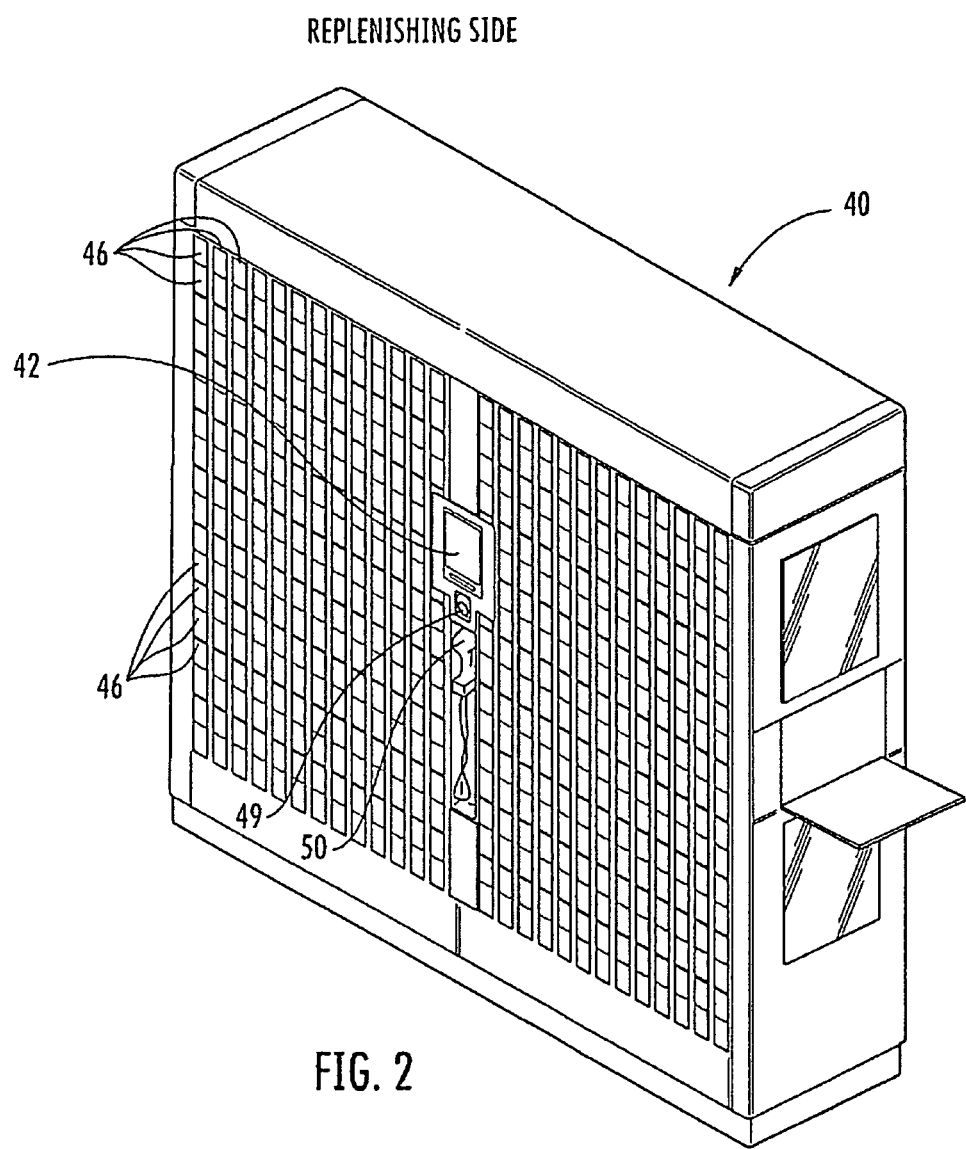
FIG. 2 is a front perspective view of an automated pharmacy machine according to some embodiments of the present invention.
Figure 3:
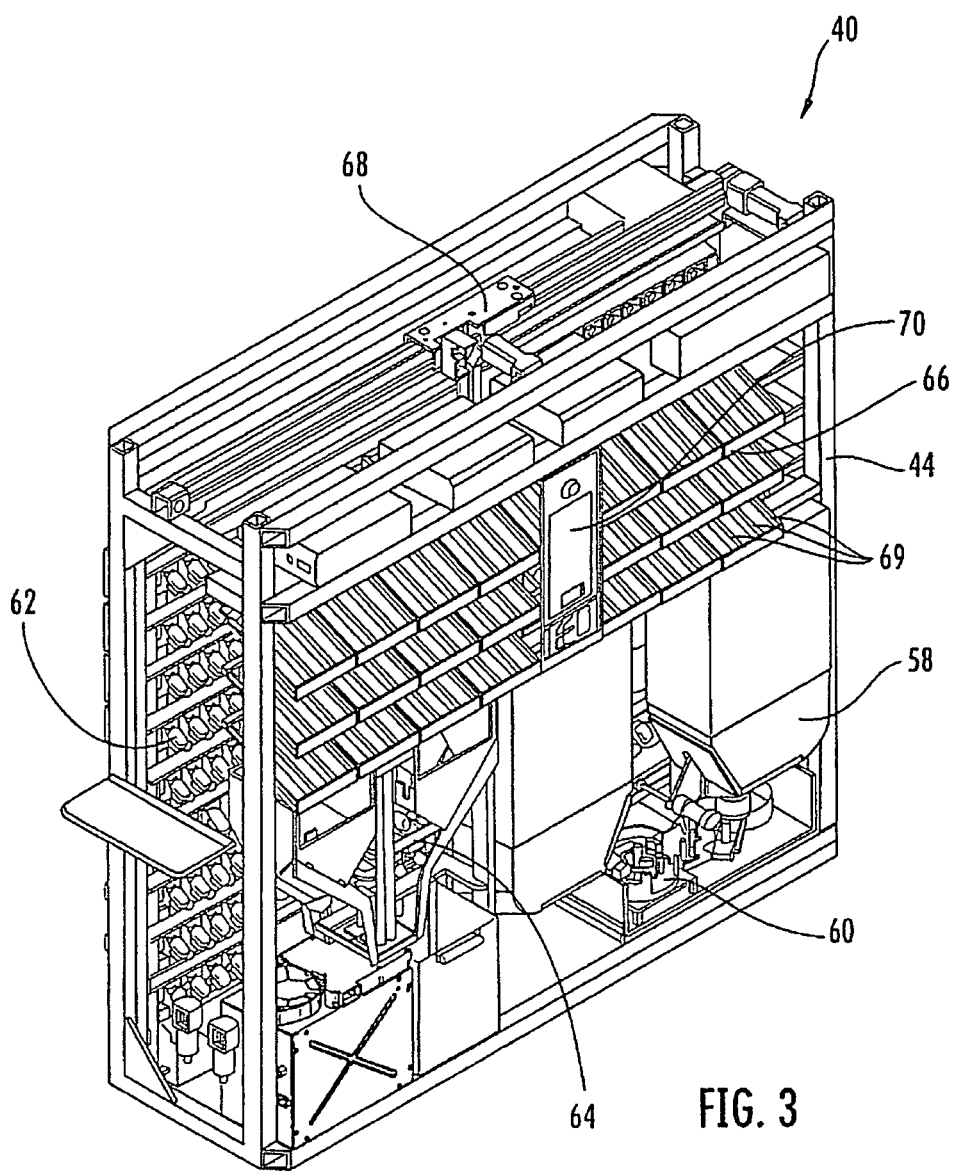
FIG. 3 is an opposite side front perspective view of the automated pharmacy machine of FIG. 2 with the outer skin removed to permit visual access to components housed therein.

A pharmaceutical dispensing apparatus that can carry out the process of FIG. 1 is illustrated in FIGS. 2 and 3 and is designated broadly therein at 40. The pharmaceutical dispensing apparatus 40 includes a support frame 44 for the mounting of its various components. The pharmaceutical dispensing apparatus 40 generally includes a processor, memory, and data storage (not shown, but which are accessible by a user via user interface monitors 42 and 70), a container dispensing station 58, a labeling station 60, a tablet dispensing station 62, a closure station 64, and an offloading station 66 including a plurality of bins 69. The processor, memory, and data storage may be utilized to control operations of the various stations as well as perform various label creation and modification functions as described herein.

In the illustrated embodiment, containers, pills and closures are moved between these stations with a single carrier or robotic arm 68. However, automated pharmaceutical dispensing machines incorporating embodiments of the present invention may utilize additional carriers/robotic arms, and in other embodiments may not utilize carrier/robotic arms at all.

The operation of the container dispensing station 58, the labeling station 60, the tablet dispensing station 62, the closure station 64, and the offloading station 66 are described in, for example, U.S. patent application Ser. Nos. 11/599,526; 11/599,576; 11/679,850; 11/693,929; 11/755,249; 11/927,865; and 11/111,270, the disclosure of each is incorporated herein in its entirety.

According to some embodiments of the present invention, monitors 42 and 70 are touch screen monitors that display GUIs that allow operators to perform various functions, including label creation and modification functions described herein. For example, an operator interacts with graphical representations (e.g., application icons) and controls (e.g., buttons, scroll bars, etc.) collectively referred to herein as GUI controls. These GUI controls perform various functions in response to physical touching by an operator (e.g., touching or tapping via a finger or stylus). GUIs displayed on each side of the pharmaceutical dispensing apparatus 40 generally relate to tasks that can be performed on the respective sides of the pharmaceutical dispensing apparatus 40. For example, an operator monitors and controls the filling of prescriptions by interacting with GUI controls displayed via the dispensing side monitor 70 (FIG. 3). An operator performs cell replenishment operations by interacting with GUI controls displayed via the replenishing side monitor 42 (FIG. 2). However, various operations may be performed by interacting with GUI controls displayed via either monitor 42, 70.

According to some embodiments of the present invention, the various GUIs share a common set of functional GUI controls. Moreover, in some embodiments, all GUI windows and screens are labeled and employ a consistent "look and feel." In addition, in some embodiments, GUI controls related to routine prescription queue management activities may be color-keyed and informative. In some embodiments, some GUI controls may appear on all toolbars and wizards displayed within the various GUIs. Other GUI controls may be context-sensitive.

The side of the pharmaceutical dispensing apparatus 40 illustrated in FIG. 2 is referred to as the "pill side" or "replenishing side." The replenishing side of the pharmaceutical dispensing apparatus 40 includes an array of cells 46, each of which is configured to store pills of a respective drug. The replenishing side of the illustrated pharmaceutical dispensing apparatus 40 also includes barcode scanners 49, 50 for scanning barcodes associated with cells 46 and with containers. The pharmaceutical dispensing apparatus 40 dispenses pills from a cell 46 to fill a particular prescription. GUIs displayed via the monitor 42 on the replenishing side are configured to display various types of information to an operator regarding the status of pill inventory in the various cells 46. In addition, various operator tasks may be performed via GUIs displayed via the replenishing side monitor 42 including, but not limited to, operations associated with replenishing cells 46 with pills, adding a new drug to inventory, setting up parameters of a cell 46, modifying parameters of cells 46, and performing return-to-stock (RTS) operations.

The side of the pharmaceutical dispensing apparatus 40 illustrated in FIG. 3 is referred to as the "pharmacist's side" or the "dispensing side." The monitor 70 on the dispensing side displays, via various GUIs, information to an operator regarding the status of prescription filling operations (e.g., pending, complete, incomplete, etc.). If a prescription filling operation cannot be completed for some reason, a GUI displays relevant information regarding this via monitor 70. In addition, various operator tasks may be performed via GUIs displayed via the dispensing side monitor 70 including, but not limited to, prescription order monitoring/processing, performing manual prescription filling, scanning out completed prescriptions, resubmitting exceptions, and performing system operations (e.g., homing/parking the robotic arm 68, configuring cells 46, running diagnostics, etc.). Manual prescription filling refers to the manual entry of a prescription into the pharmaceutical dispensing apparatus 40. Prescription processing is monitored and managed from the dispensing side of the pharmaceutical dispensing apparatus 40. An operator monitors and controls the filling of prescription orders by touching various GUI controls in the GUIs displayed on the dispensing side monitor 70.

Embodiments of the present invention provide software components, referred to as a label wizard, that are responsible for the creation of a label bitmap (or other type of image) to be printed on a label. In some embodiments, these software components may be embedded in a control application and locally hosted, while in other embodiments these components may reside on external devices (e.g., PCs, etc.). In other words, in some embodiments a label wizard may reside and execute entirely on a single device, such as a personal computer (PC) or a pharmaceutical dispensing apparatus 40. In other embodiments, portions of a label wizard may reside and execute on two or more separate devices.

According to embodiments of the present invention, pharmaceutical dispensing apparatus 40 includes a label wizard that executes via a processor (500, FIG. 25) associated with the pharmaceutical dispensing apparatus 40 (FIGS. 2-3) and that allows a user to create and modify labels for pill containers (vials), cells 46, and dispensing bins 69. With respect to labels for vials, the label wizard enables an operator of the pharmaceutical dispensing apparatus 40 to create and/or modify a label designed to be used for prescription orders filled by the pharmaceutical dispensing apparatus 40. With respect to labels for cells 46 and dispensing bins 69, the label wizard enables an operator of the pharmaceutical dispensing apparatus 40 to create and/or modify labels based on information entered by an operator and/or from data storage. The various GUIs associated with the label wizard are typically displayed via the dispensing side monitor 70, but may be displayed via the replenishing side monitor 42 in some embodiments.

Typically, a pharmacy will design a label format that will be used for all of the prescriptions that come through the pharmaceutical dispensing apparatus 40, or for a limited number of labels to be used for particular prescriptions. However, if a pharmaceutical dispensing apparatus 40 is being used to fill prescriptions for different pharmacies, each pharmacy might have its own label format. Thus, the label wizard described herein is not utilized during prescription fulfillment operations of an automated or semi-automated pharmaceutical dispensing system, but rather during an initial design of a label or during modification of a label.

Figure 4:
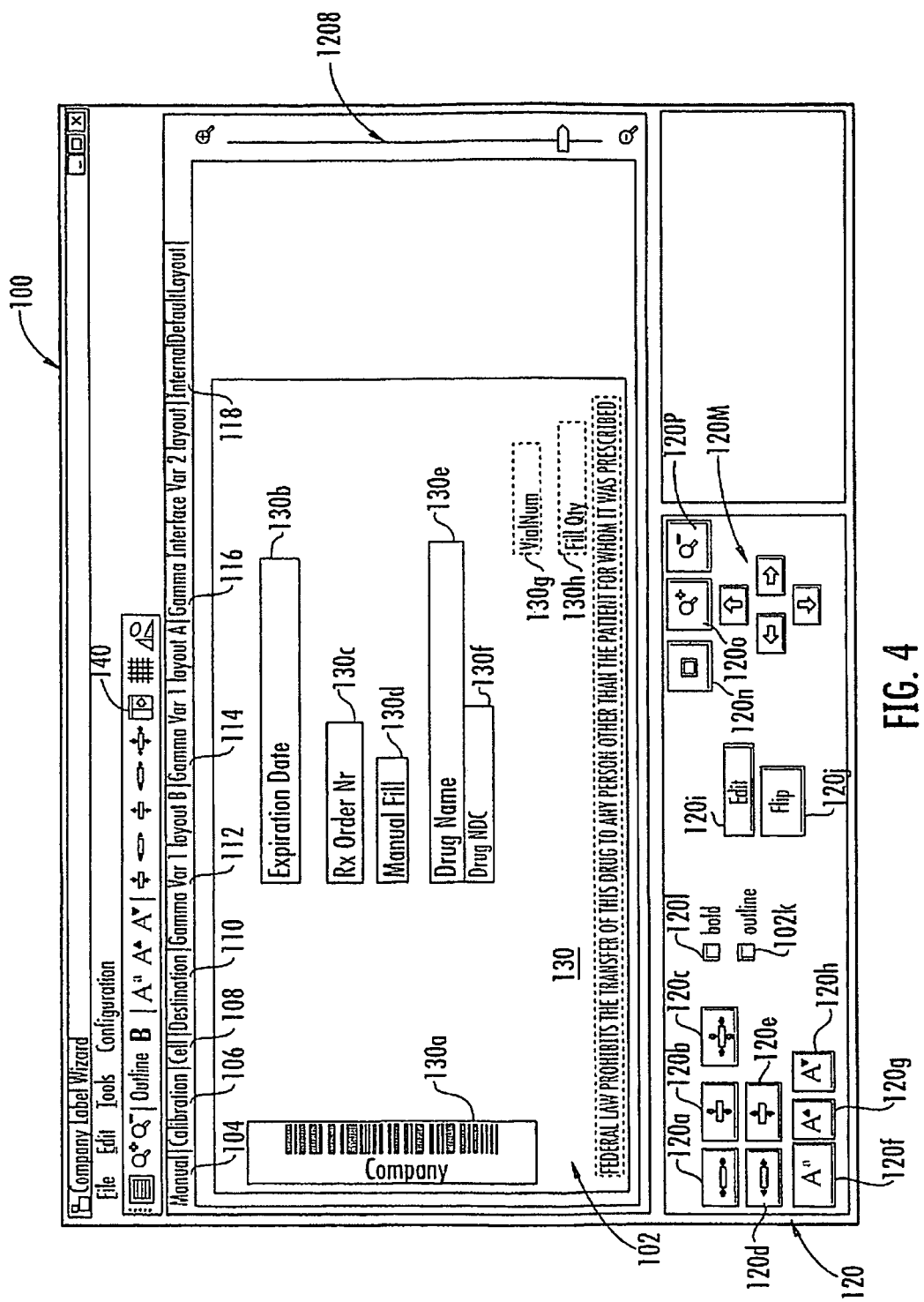

Referring to FIG. 4, the label wizard main GUI 100 that allows a user to create and modify labels is illustrated. The label wizard main GUI 100 includes a label template display area 102, a series of label selection tabs 104-118 positioned above the label template display area 102, and a plurality of GUI controls 120a-120p located in toolbox area 120, which is positioned below the label template display area 102. Label selection tab 104, when selected by a user, allows the user to create a label for a manual prescription order. A manual prescription order is one entered directly into the pharmaceutical dispensing apparatus 40 by an operator as opposed to one received electronically from the pharmacy host system, a remote physician or other healthcare provider.

Label selection tab 106, when selected by a user, allows the user to create a label for use in filling calibration prescription orders. A calibration prescription order is part of a testing routine utilized to ensure the dispensing accuracy of an automated pharmacy machine.

Label selection tab 108, when selected by a user, allows the user to create a label for a cell 46 on the replenishing side of the pharmaceutical dispensing apparatus 40. Label selection tab 112, when selected by a user, allows the user to create a label for a dispensing bin 69 on the dispensing side of the pharmaceutical dispensing apparatus 40. The remainder of the label selection tabs 112-118 allow a user to create various custom labels.

The label wizard will now be described with respect to creating and modifying labels for vials. However, all the functionality described herein may also be utilized with respect to creating and modifying labels for cells 46 and dispensing bins 69. The label wizard creates an image, such as a bitmap, that can be printed on an actual label.

In the illustrated label display area 102 of the label wizard GUI 100, a label template 130 is displayed for a vial label that is being constructed or modified. The illustrated label template 130 includes various data fields 130a-130h positioned thereon in locations where actual information they represent would appear on an actual printed label. Each data field displayed within the label template 130 can be manipulated and configured easily. For example, a user can easily move a data field to a desired location on the template 130 by touching the data field and dragging the data field with a finger or stylus. Similarly, a user can select a data field by touching the data field and then configuring various parameters (e.g., font, style, color, etc.) of the selected data field via various GUIs and GUI controls described and illustrated herein.

FIG. 5 illustrates a list of data fields that can be used to build/modify a label within label template 130 of FIG. 4, according to some embodiments of the present invention. Referring back to FIG. 4, in the illustrated label template 130, data field 130a is configured to include barcode data that identifies a vial in a prescription order. Data field 130b is configured to display the date that the particular drug expires. Data field 130c is configured to contain the prescription order number. Data field 130d is configured to display information indicating that a label produced by this particular label template 130 is associated with a manual prescription order and not an automatic prescription order by the pharmaceutical dispensing apparatus 40. Data field 130e is configured to display the name of the drug in the vial for which the label is to be attached. Data field 130f is configured to display the National Drug Code (NDC) number, Drug Identification Number (DIN), or other code for the particular drug. Data field 130g is configured to display the number of the vial, i.e., in the situation where multiple vials are required to fill a single prescription order. Data field 130h is configured to display the quantity of pills actually contained in the particular vial that a label produced by the label template 130 is to be attached.

Still referring to FIG. 4, GUI controls 120a-120e are scaling controls that allow a user to adjust the size of a data field displayed within the label template 130. GUI controls 120f-120h are font type and size GUI controls that allow a user to adjust the font type and font size of characters displayed within the various data fields. As would be understood by one skilled in the art, a user selects or activates a data field by touching the data field, selects the characters within the activated data field to be modified, and then touches one or more of the GUI controls 120a-120h to adjust various aspects of the displayed characters.

GUI control 120i is configured to open an edit wizard to allow an operator to modify an existing label. The edit wizard will be described below. GUI control 120*j* allows a user to change the orientation of a data field. For example, a selected data field can be rotated in 90 degree (or other) increments in response to user touching of GUI control 120*j*. GUI control 120*k* and GUI control 120*l* can be selected to display text within a data field in outline font and in bold type, respectively. GUI controls 120*m* are configured to incrementally move a selected data field up, down, left, right, respectively, within label template 130. GUI controls 120*n*, 120*o* and 120*p* are zoom controls that allow an operator to enlarge and reduce the display of a selected data field within the template 130, for example, for ease of editing a particular data field. In addition, a slider GUI control 120*q* is located along the right-hand side of the display area 102 and allows a user to enlarge and decrease the display of the label template 130.

GUI control 140, when touched by a user, displays a list of available data fields. An exemplary list is displayed in FIG. 5. A user selects data fields from the list to build a label via the label template 130, as will be described below.

Figure 6:
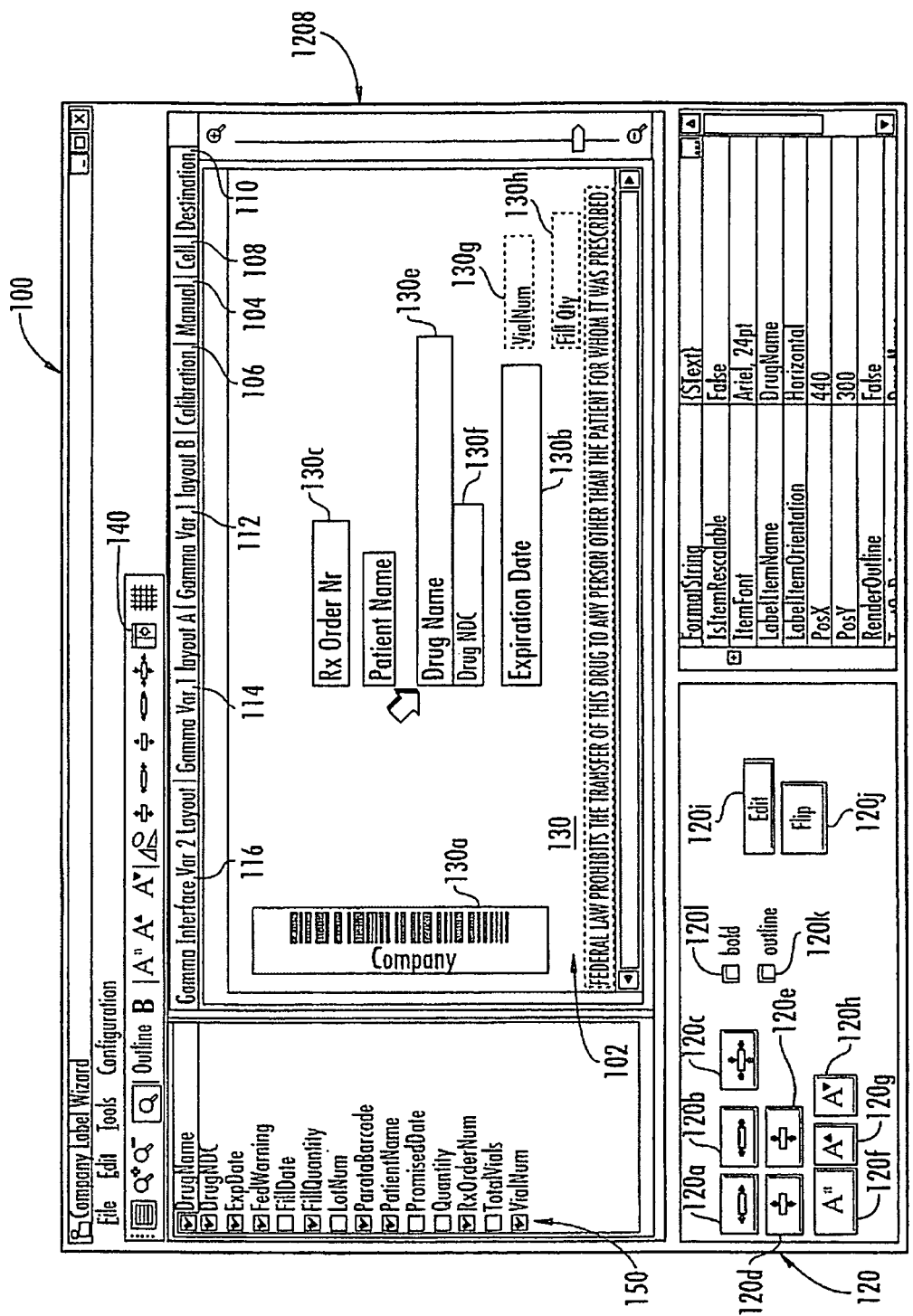
Figure 7:
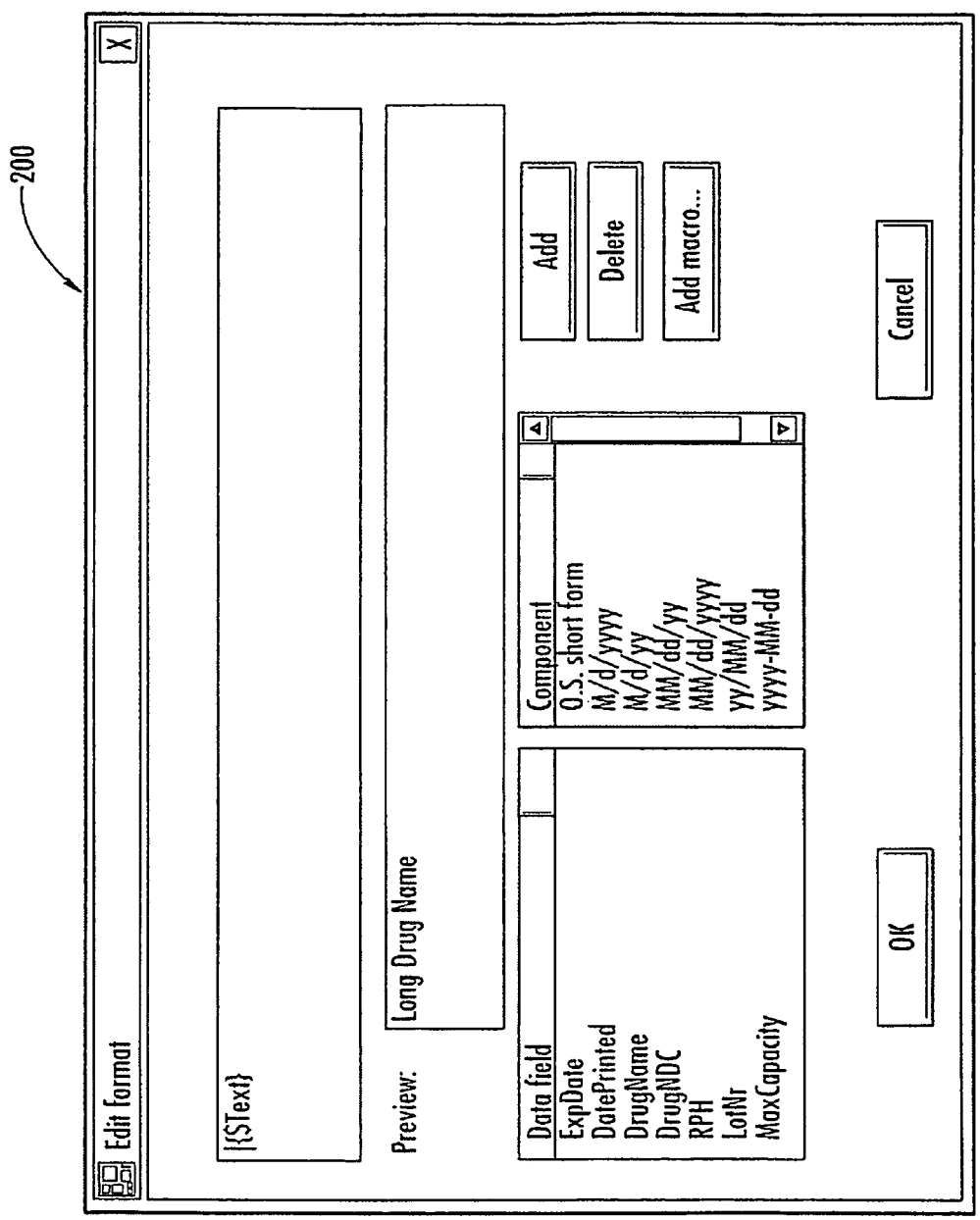
Figure 22:
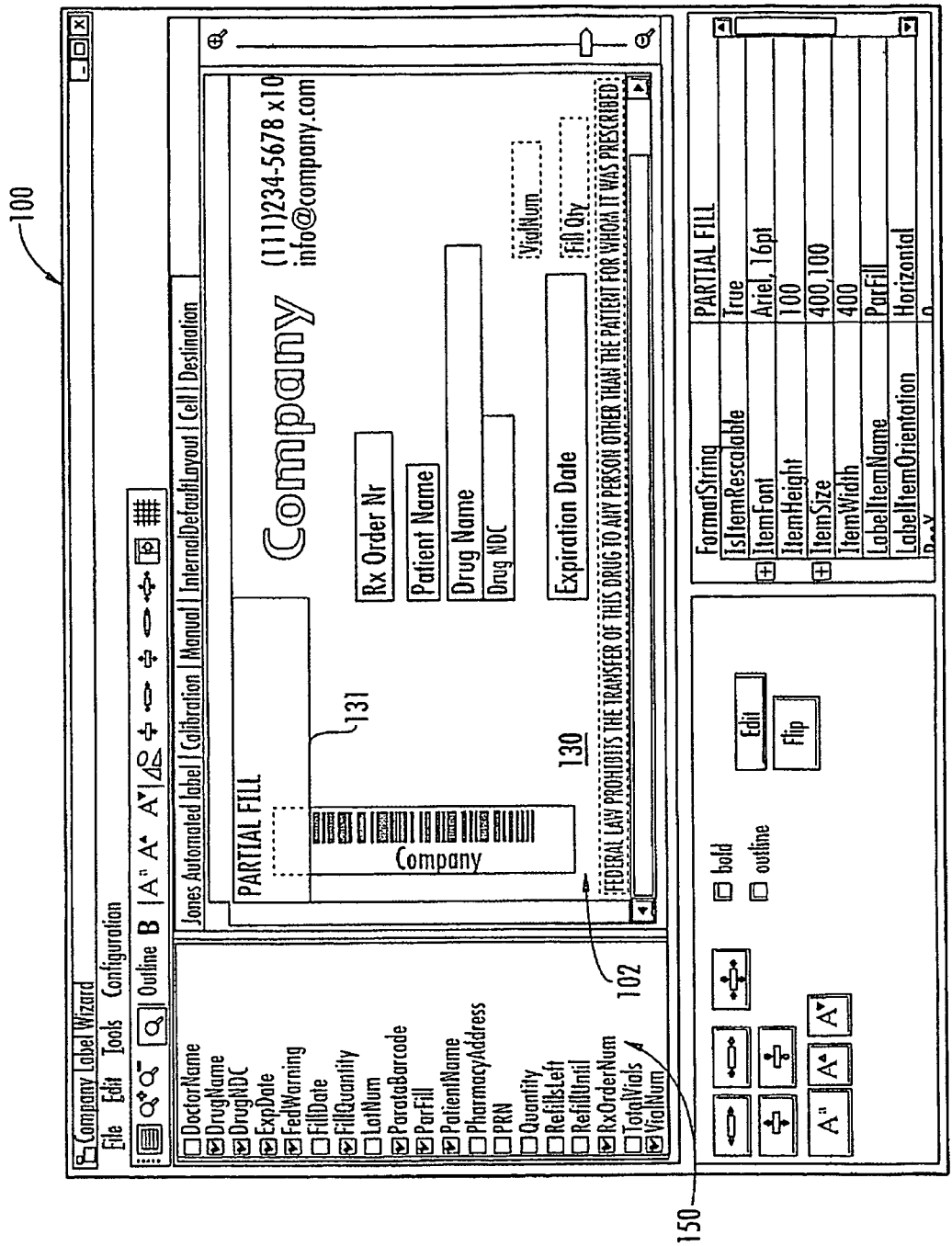

Referring now to FIG. 6, a user has activated GUI control 140 and a list of available data fields is displayed in display area 150. In the illustrated embodiment, display area 150 is to the left of label display area 102. However, embodiments of the present invention are not limited to the illustrated orientation of display area 150 and label display area 102. Display area 150 and label display area 102 may be positioned relative to each other in any of a number of ways, without limitation. Data fields currently used in the label template 130 are indicated with checkmarks, as illustrated. To delete a data field from the label template 130, a user de-selects the checkbox (i.e., via touching the respective checkbox) associated with the particular data field. The data field is then automatically removed from the label template 130. To add a data field, a user selects the checkbox (i.e., via touching the respective checkbox) next to the particular data field that is to be added to the label template 130. The data field will appear in the top left corner of the label template 130 (e.g., as illustrated in FIG. 22). The user drags the added data field to a desired location in the label template 130 using a finger or stylus. The data field can then be configured using the edit format GUI 200 illustrated in FIG. 7, which is displayed in response to a user touching GUI control 120*i*. FIGS. 8A-8D list exemplary components, macros, and procedures associated with data fields that can be configured using the edit format GUI 200. The components, macros, and procedures listed in FIGS. 8A-8D define how data is treated and/or behaves within a respective data field. For example, the data field "DatePrinted" will only allow the actual date a label is printed to be entered, and no other date.

A scripting language is utilized to transform the data about a prescription order into information to display within the label display area 102. According to embodiments of the present invention, a data field is a string that indicates a reference to a piece of data; it assumes the form of {[@FieldName]$ComponentName[:Format]} and is resolved at rendering time. According to embodiments of the present invention, a macro is a procedure that accepts a defined number of expressions as comma separated parameters and returns an expression. Macros, for example, may include just about anything to manipulate a piece of text. According to embodiments of the present invention, macros are preceded by the pound symbol and have their arguments listed between parenthesis such as #MACRO (arg1 arg2). Macros are resolved at rendering time. Scripting languages, data fields, and macros are well understood by those skilled in the art and need not be explained further herein.

A label wizard, according to embodiments of the present invention, maintains a list of the available data which is published by a host interface application on a host vendor/customer basis. This includes which label items are to be made available. A pharmaceutical dispensing apparatus 40 is capable of maintaining different label layouts for different groups of prescriptions to be filled (e.g., for different pharmacies, etc.).

Such 'data about data' (metadata) contains information that will aid the user into preparing an appropriate layout; for instance, if a field is expected to have a maximum length of 50 characters, the proposed size of the label item in the label template 130 is sized accordingly so that the user will know that the field requires a lot of room. Also, a sample of data can be provided and can be used in the label displayed in a preview GUI (e.g., GUI 360, FIG. 16). This sample data can be editable to allow the user to test the output (i.e., a label's appearance) under different inputs.

In addition to the label items declared from the host interface, the user can manually create new ones based on the metadata made available. A single label item can import data from any number of data fields. Data is not limited to text, but it may include raster bitmaps. The metadata will differentiate between embedded bitmap, for which every order will contain a serialized version of the bitmap, and referenced bitmaps, for which the order will contain the location of the bitmap on an accessible path. Label items containing bitmaps have special operations for image manipulation such and cropping, scaling. The host interface may request that multiple label layouts are to be made available, for instance in a pharmaceutical dispensing apparatus 40 filling prescription for more than one pharmacy, each of the pharmacies having their own label layout. Another example of this scenario is when multiple layouts are to be created to handle different versions of the same label in different languages. When filling the order, the host interface declares which label layout has to be used to create the label that will be applied to the vial. According to some embodiments of the present invention, the arrangement of the items in a particular layout can be copied to another layout to minimize the necessity of manually preparing multiple layouts similar to one another.

According to some embodiments of the present invention, the text displayed on a label can include conditional logic as defined by the formal language described above such as: "If the script is PRN display 'May refill until mm/dd/yy', otherwise display 'X refills before mm/dd/yy' or 'No refills left' if the number of refills is zero." Conditional logic for data fields is well understood by those skilled in the art and need not be described further herein.

According to some embodiments of the present invention, when editing the format of a label, e.g., via GUI 360 (FIG. 16), a preview area will provide an as-you-go example of what the output of the label item will be like when printed on the label.

According to some embodiments of the present invention, it is possible to import a bitmap or other image to be displayed as a background on a label to help the user arrange the label items, and/or for other reasons.

According to some embodiments of the present invention, labels may be associated with a language and/or culture (e.g., American English) to correctly format specific items (such as dates) or general label format (such as specific alignment of text). The label wizard can represent any human language supported by the UNICODE standard.

Figure 9:
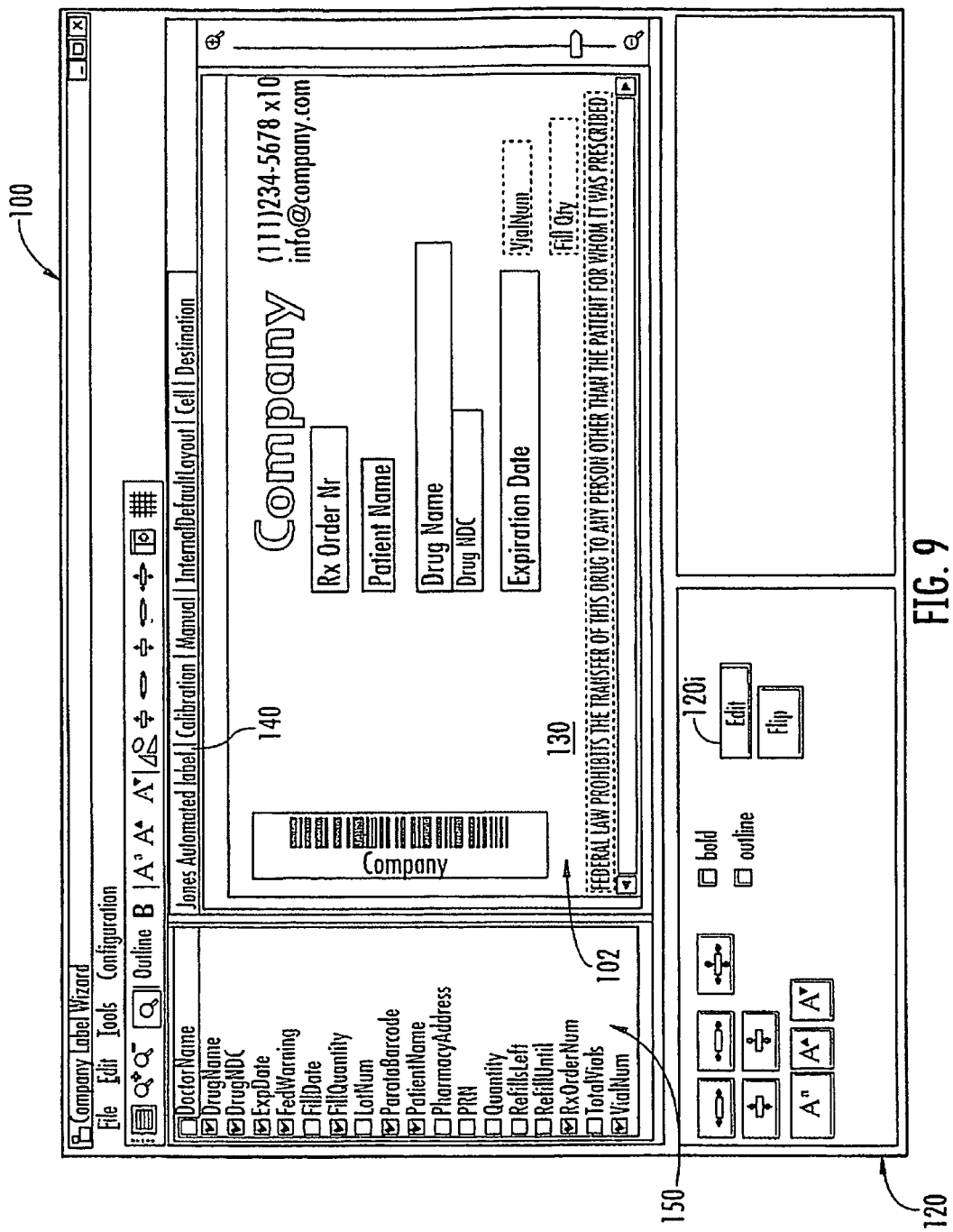
Figure 10:
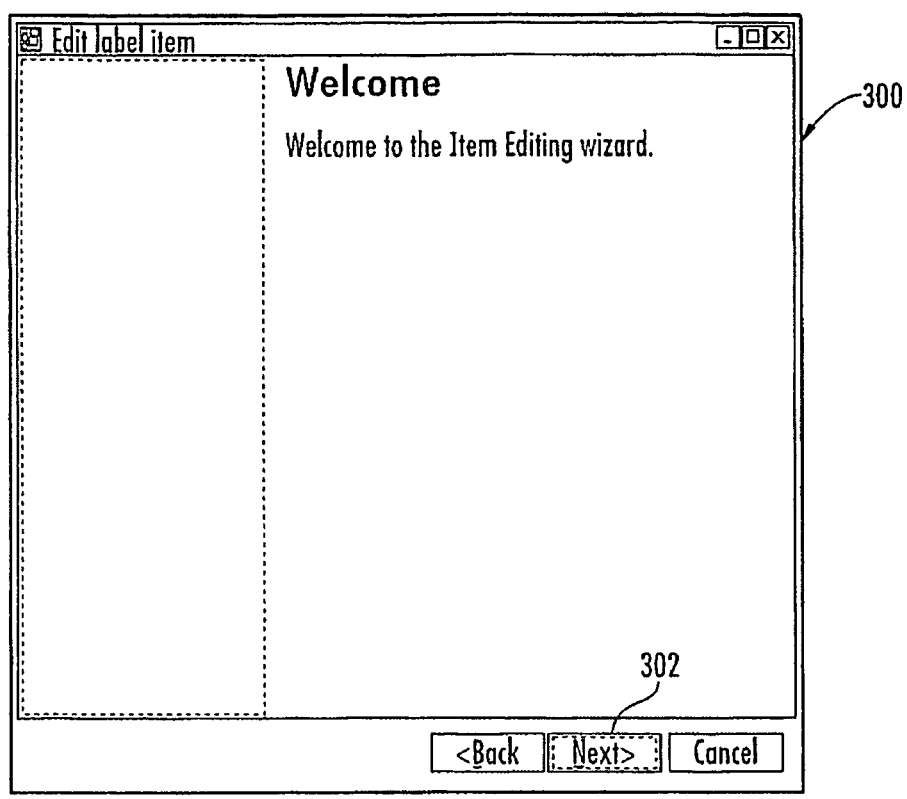
Figure 11:
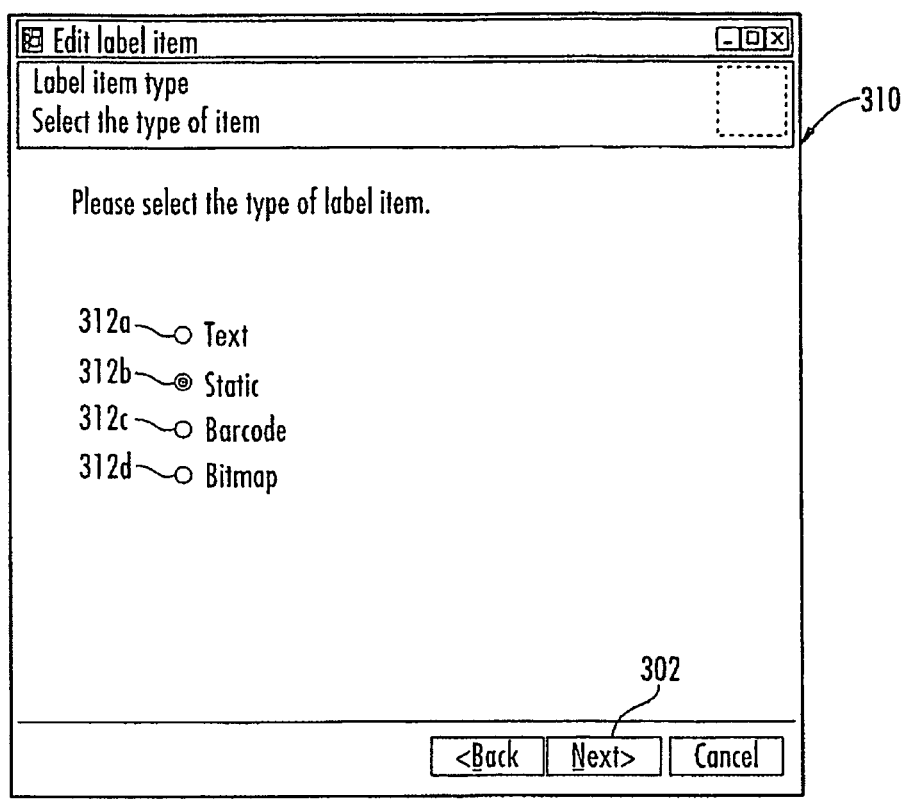

Referring now to FIGS. 9-24, operations for modifying an existing label using a label wizard, according to some embodiments of the present invention, will now be described and illustrated in detail. As an example, a pharmacy wants to display the words "Partial Fill" on an existing label that the pharmacy uses for particular prescription orders. In order to add "Partial Fill," a new data field needs to be added to an existing label. A user opens the label wizard main GUI 100 and selects the particular label to be modified via the label selection tabs above the display area 102. In the illustrated embodiment, label selection tab entitled "Jones Automated Label" 140 (FIG. 9) is selected to display a label template 130 associated with a particular label. To add the new data field, a user touches the edit GUI control 120*i* to open a new item wizard, and which displays an initial GUI 300, as illustrated in FIG. 10. Upon touching the "Next" button 302 at the bottom of GUI 300, label item type GUI 310 is displayed, as illustrated in FIG. 11. Within label item type GUI 310, a user selects the type of item to be added as a data field from radio buttons 312*a*-312*d*. In this particular example, the user has selected a static label item via radio button 312*b*.

Figure 12:
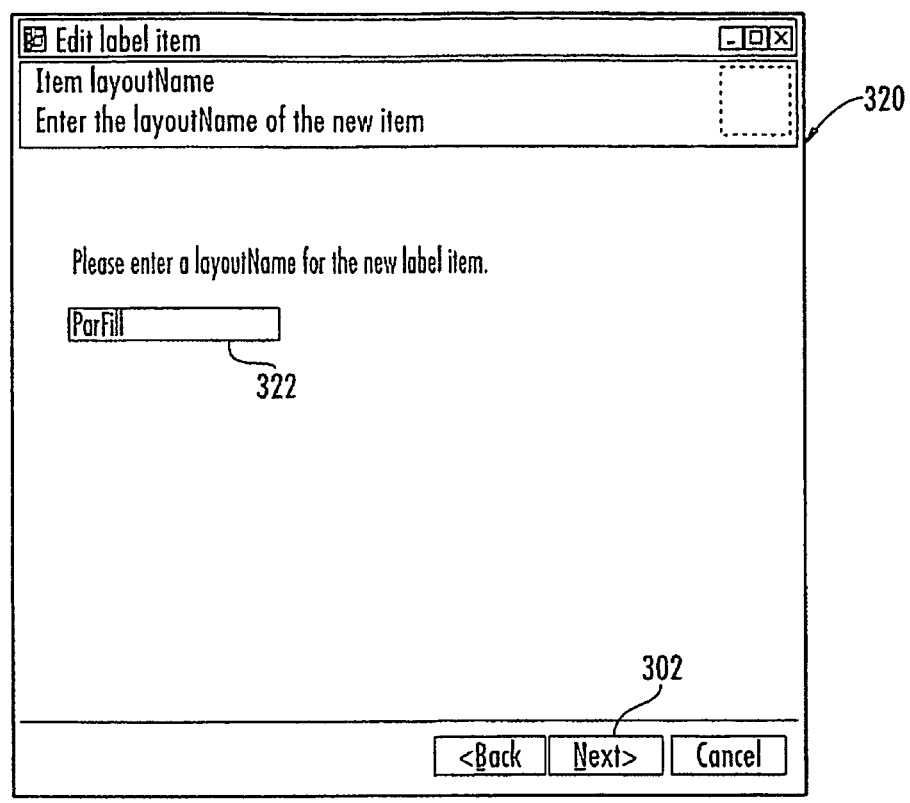

Upon touching the "Next" button 302, item layout name GUI 320 is displayed, as illustrated in FIG. 12. In the displayed GUI 320, a user enters the name of the data field to be added in box 322. In the illustrated example, the user has entered "ParFill" in box 322. The user enters this text in this box (and subsequent boxes) via a keyboard or keypad associated with and/or in communication with the pharmaceutical dispensing apparatus 40. In some embodiments, a touch keyboard/keypad may be displayed within GUIs within which text is being entered, etc.

Figure 13:
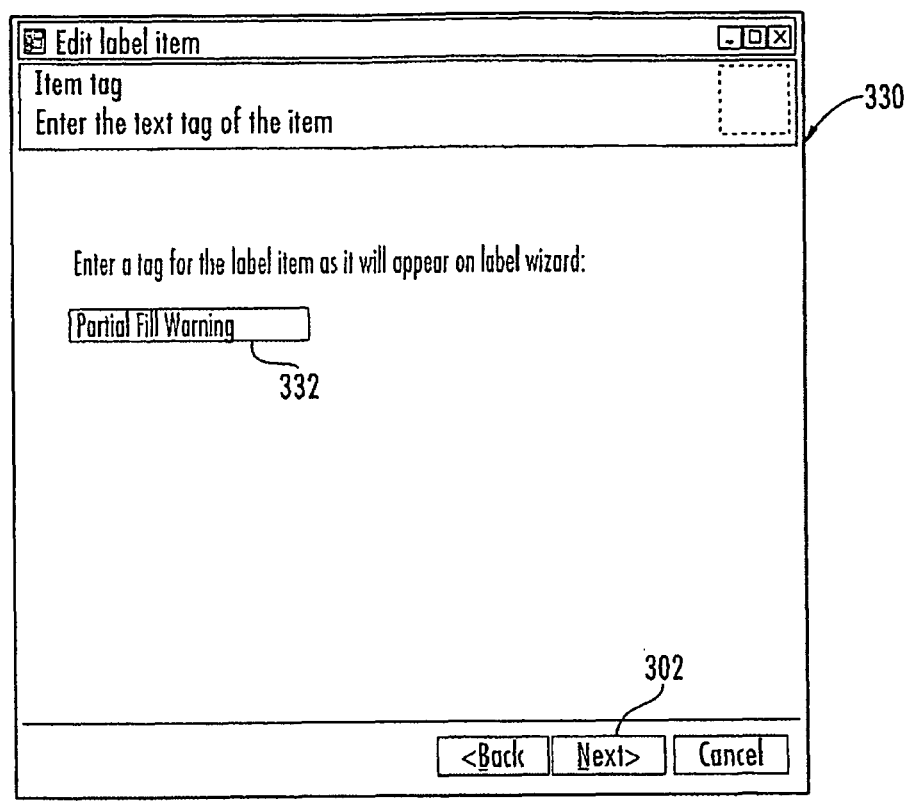
Figure 14:
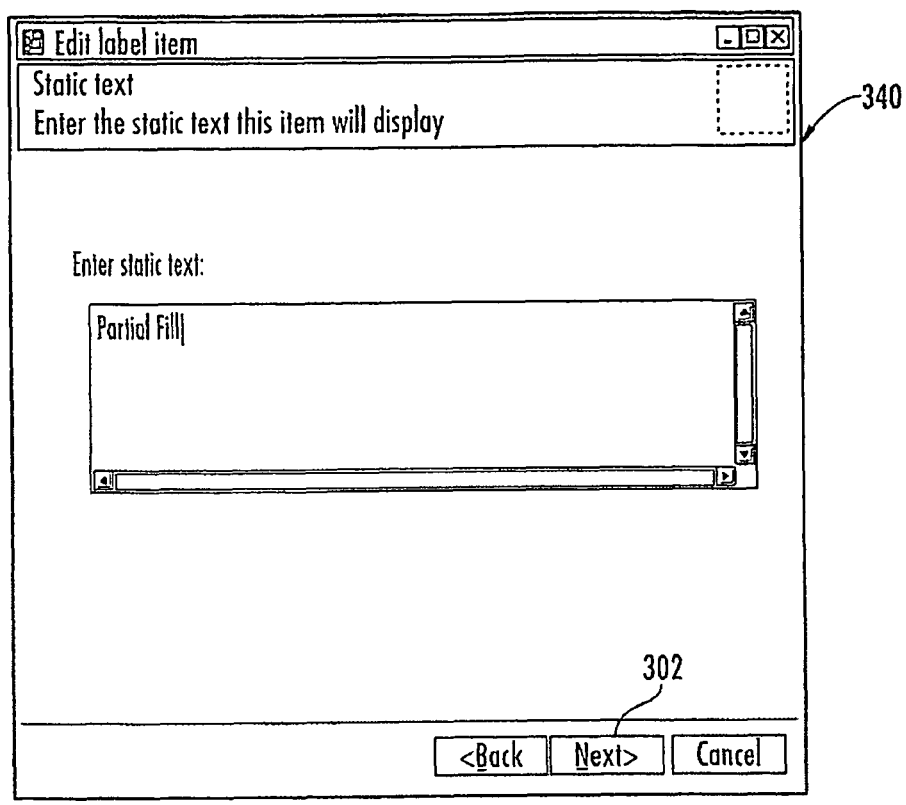
Figure 15:
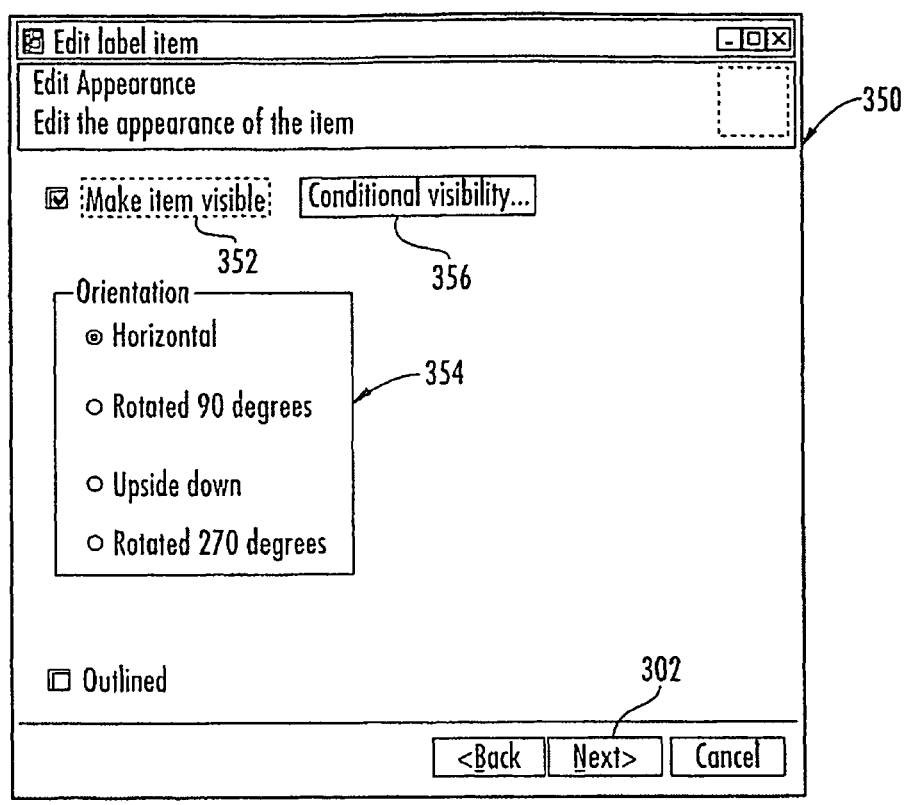

Upon touching the "Next" button 302, item tag GUI 330 is displayed, as illustrated in FIG. 13. In item tag GUI 330, a user enters a tag within box 332 for the data field as it will appear in the label template 130. In this example, the user enters "Partial Fill Warning" in box 332. Upon touching the "Next" button 302, static text GUI 340 is displayed, as illustrated in FIG. 14. In the static text GUI 340, the user enters the text to be displayed on the actual label that will be printed for the new data field. In this example, the user enters the words "Partial Fill" in box 342. Upon touching the "Next" button 302, the edit appearance GUI 350 is displayed, as illustrated in FIG. 15.

Figure 16:
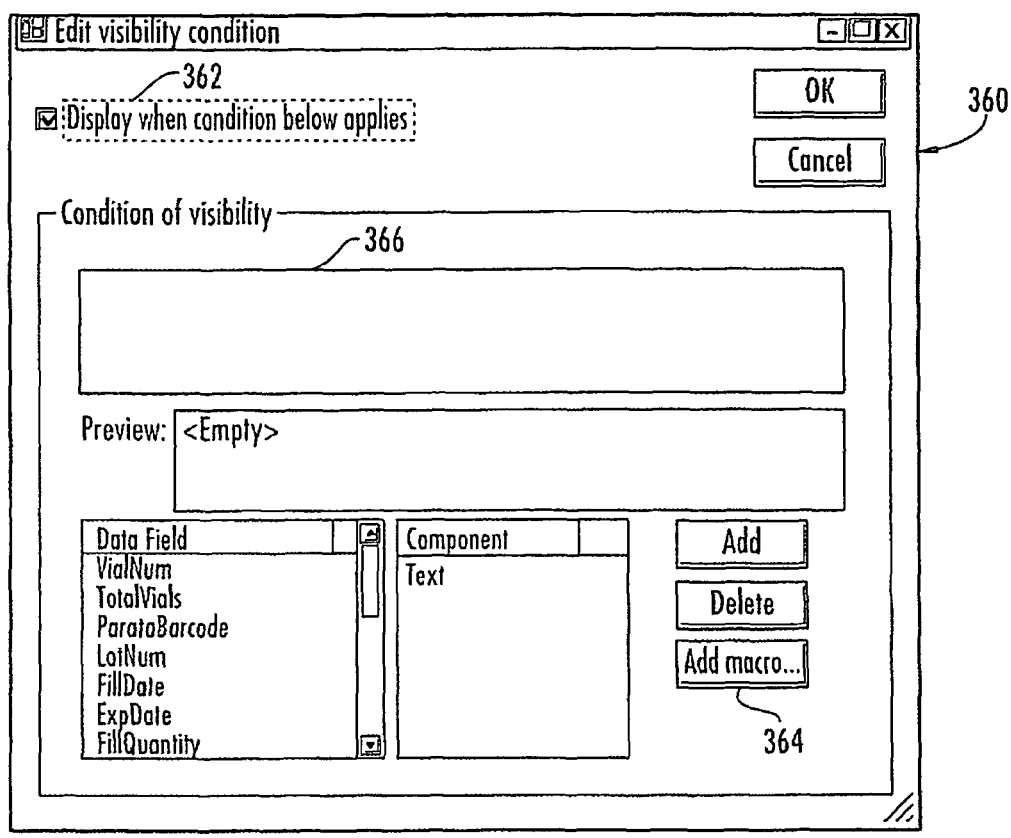
Figure 17:
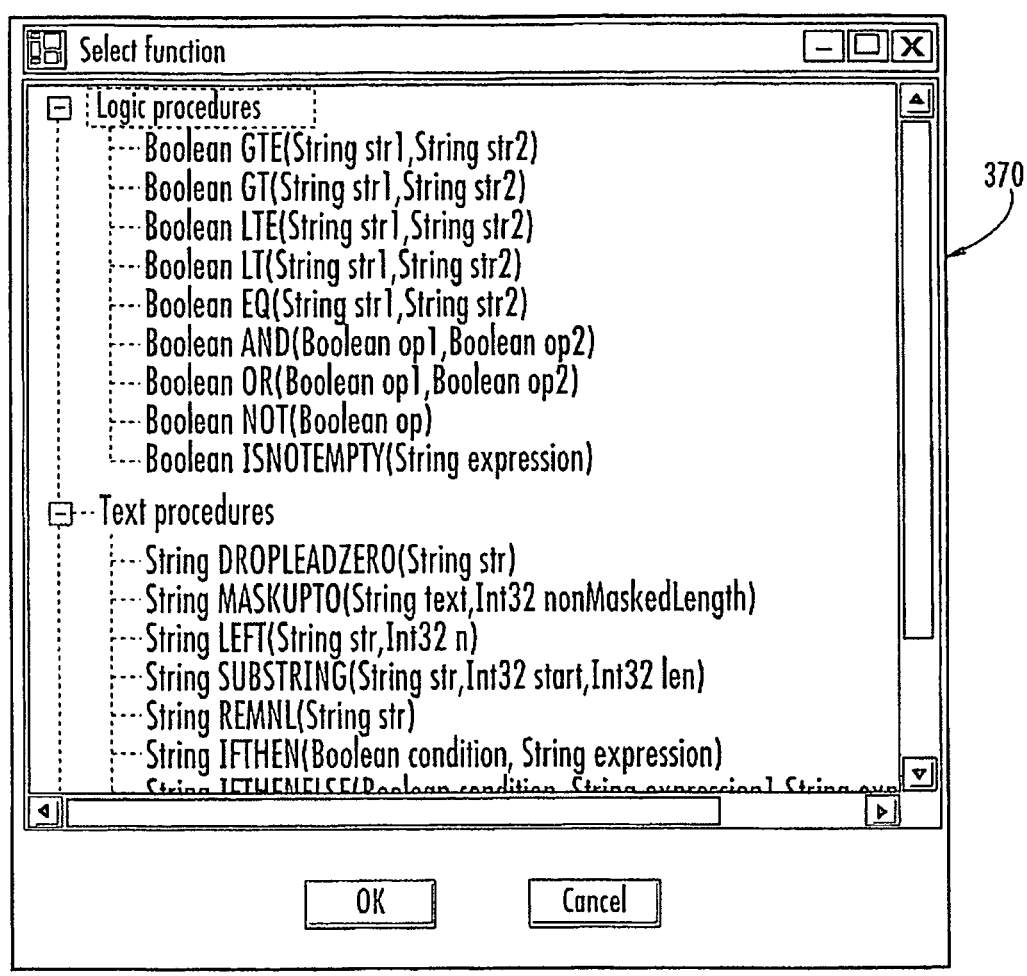

In the edit appearance GUI 350, the user has selected the make item visible GUI control 352. The user has also indicated, via radio button GUI controls 354, that the orientation of the new data field is to be horizontal. The edit appearance GUI 350 includes a conditional visibility GUI control 356. Upon touching the conditional visibility GUI control 356, the edit visibility condition GUI 360 is displayed, as illustrated in FIG. 16. In the edit visibility condition GUI 360, the user has selected GUI control 362 ("Display when condition below applies"). Box 366 will display the condition of visibility as described below. Upon touching the GUI control 364 ("Add macro"), the select function GUI 370 is displayed, as illustrated in FIG. 17.

Figure 18:
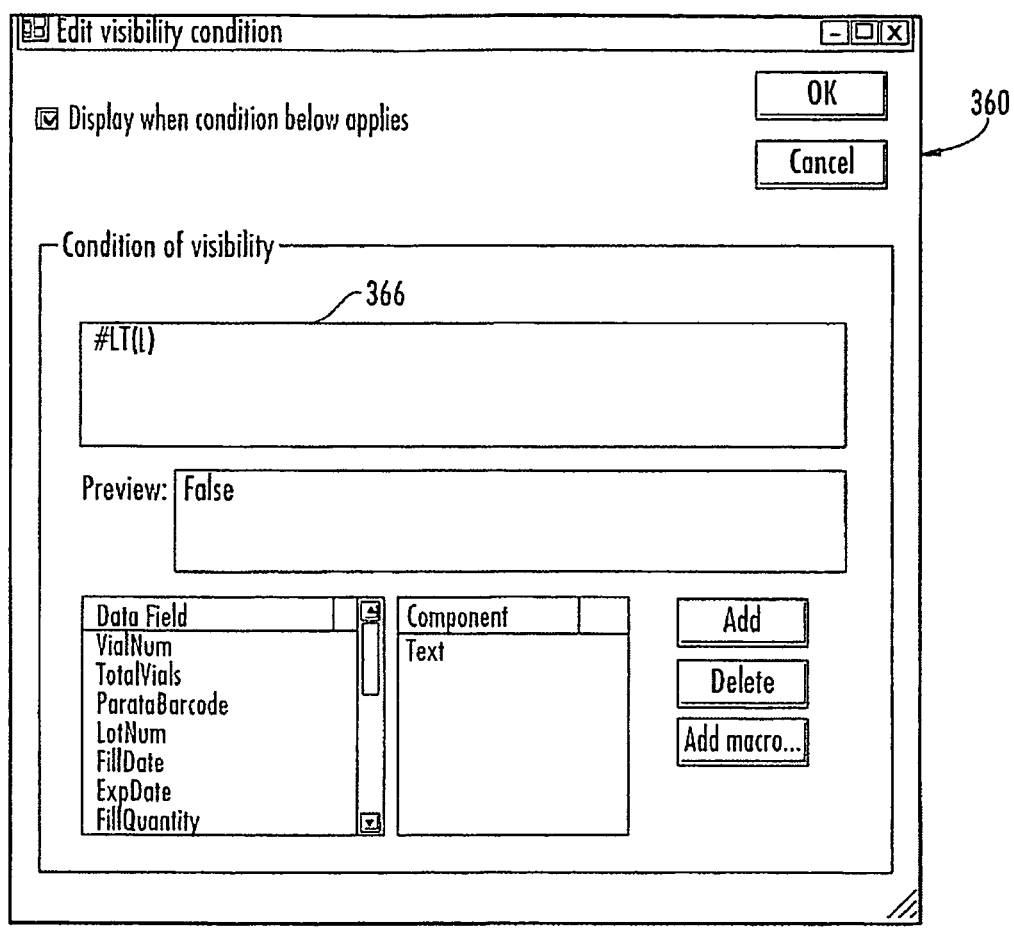
Figure 19:
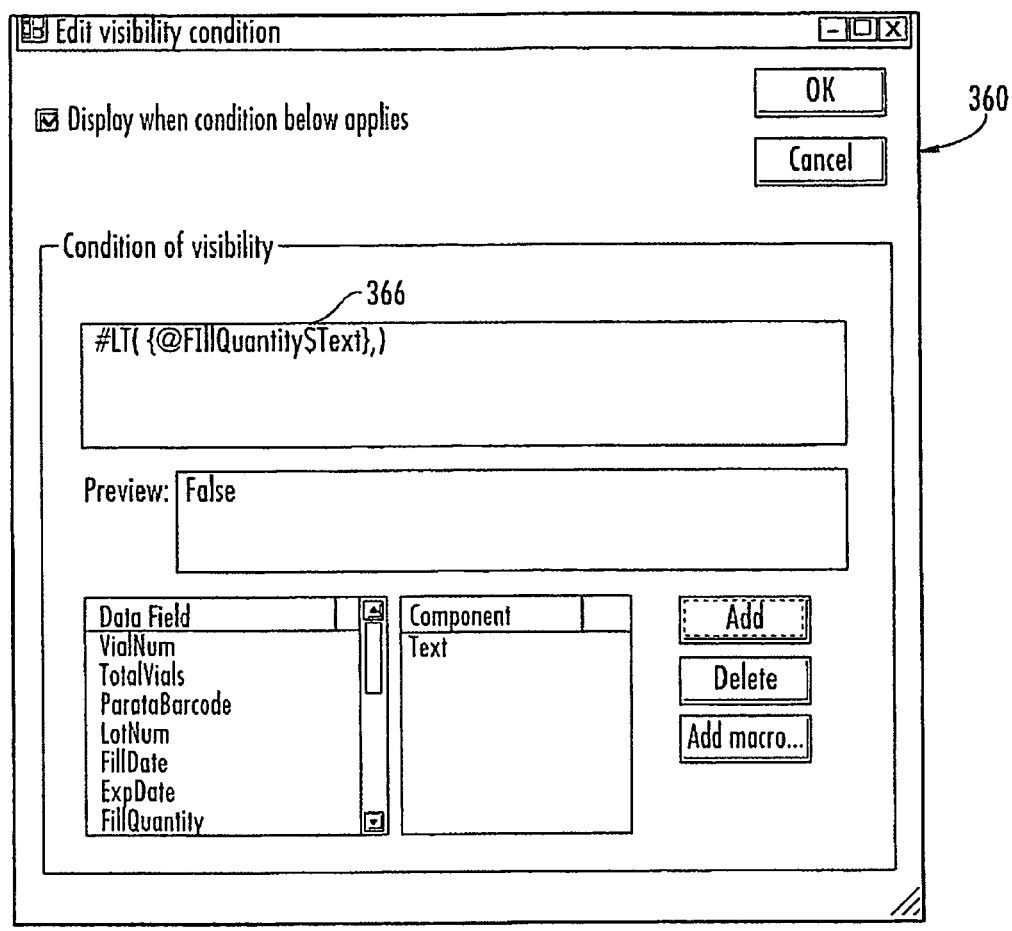
Figure 20:
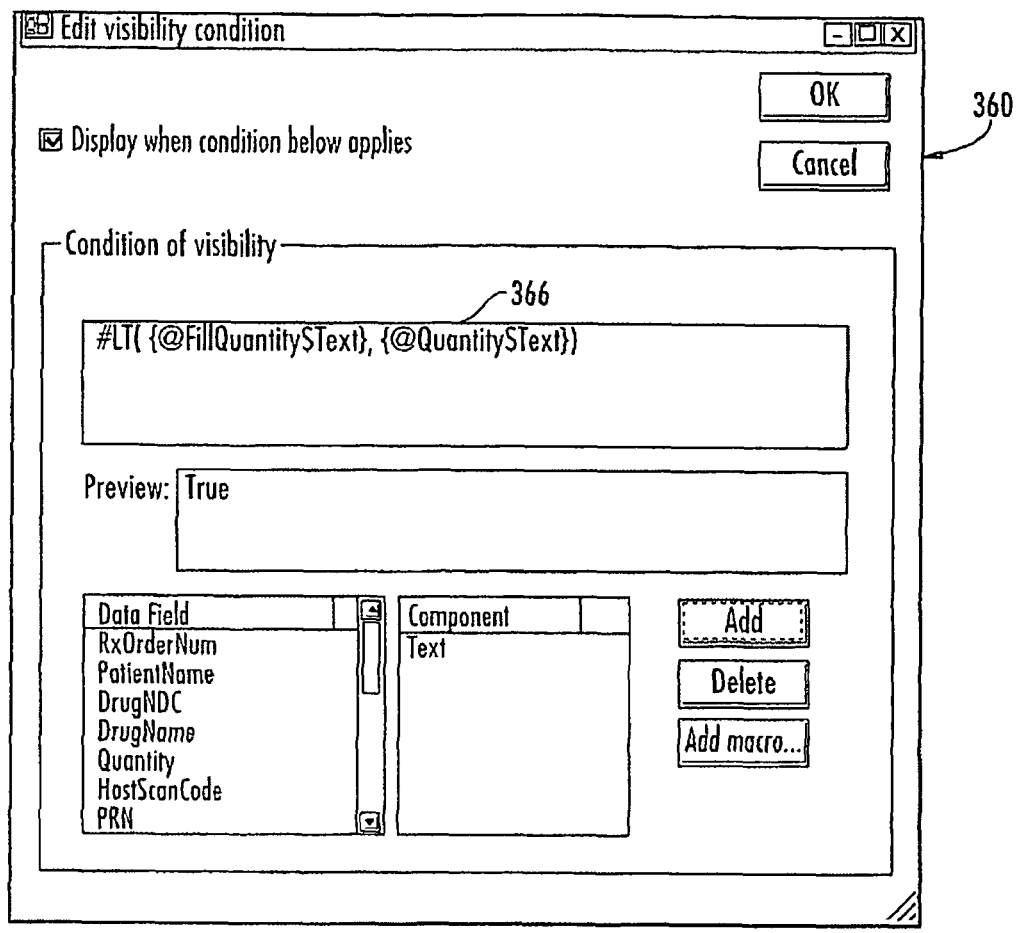
Figure 21:
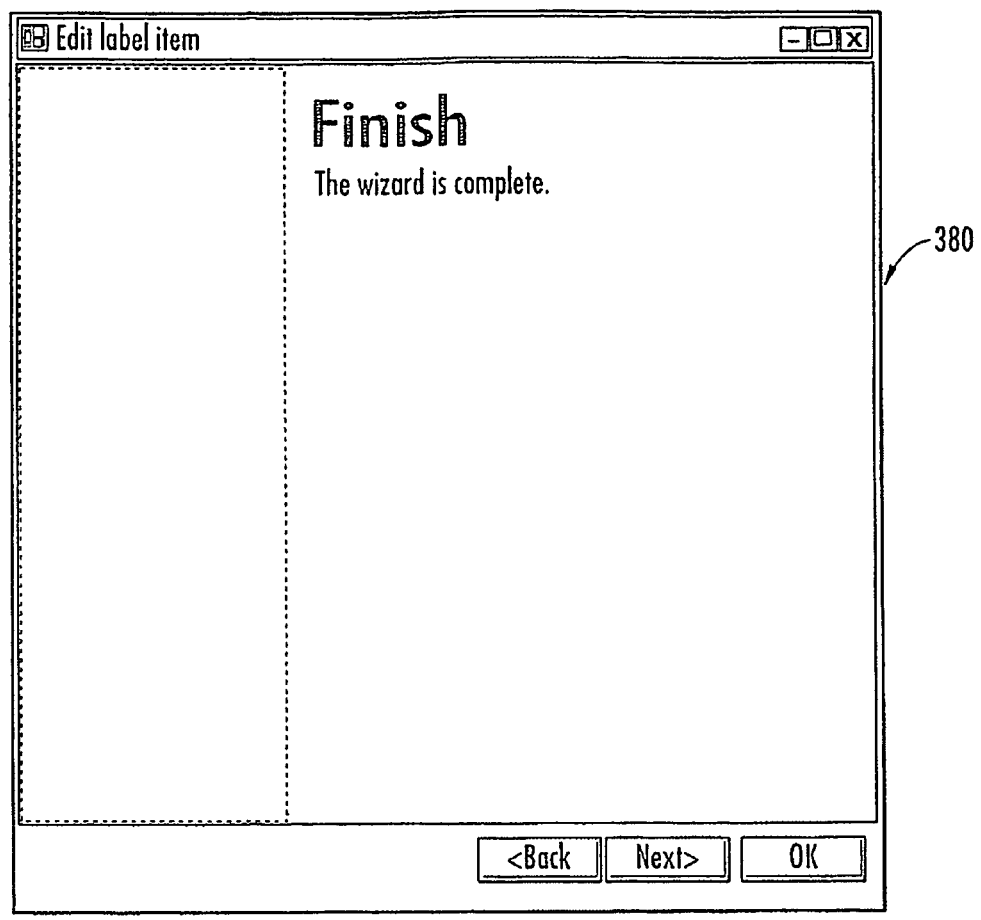

In the select function GUI 370, the user selects a macro function to be associated with the new data field. As illustrated in FIGS. 18-20, the user utilizes the edit visibility condition GUI 360 to define various conditions associated with the display of the new data field. The condition of visibility is displayed in box 366. Upon completion, finish GUI 380 is displayed, as illustrated in FIG. 21. Upon touching the "OK" button 382, the label wizard main GUI 100 is displayed and the new data field 131 appears in the list in display area 150 and on the label template 130 in the upper left-hand corner, as illustrated in FIG. 22.

Figure 23:
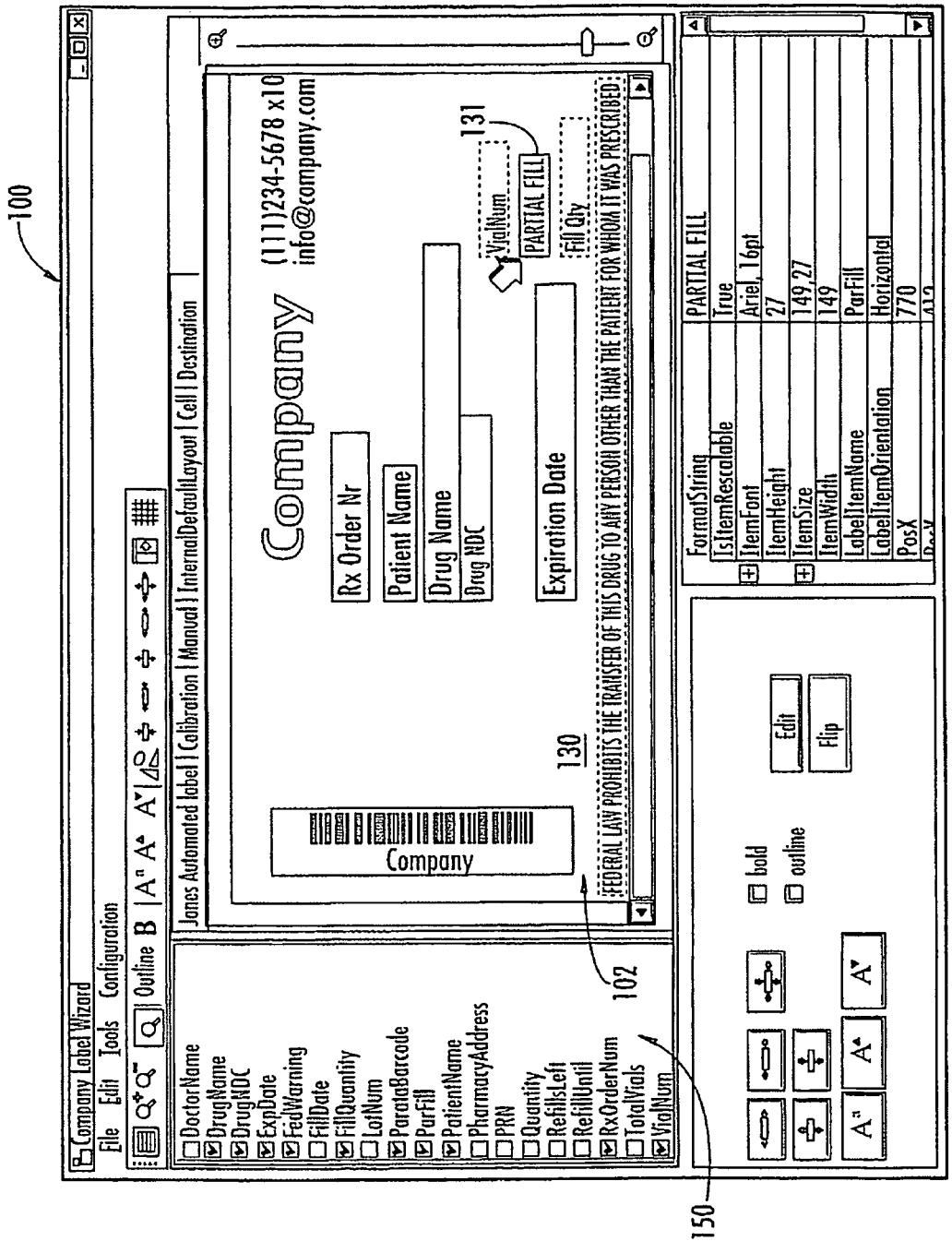
Figure 24:
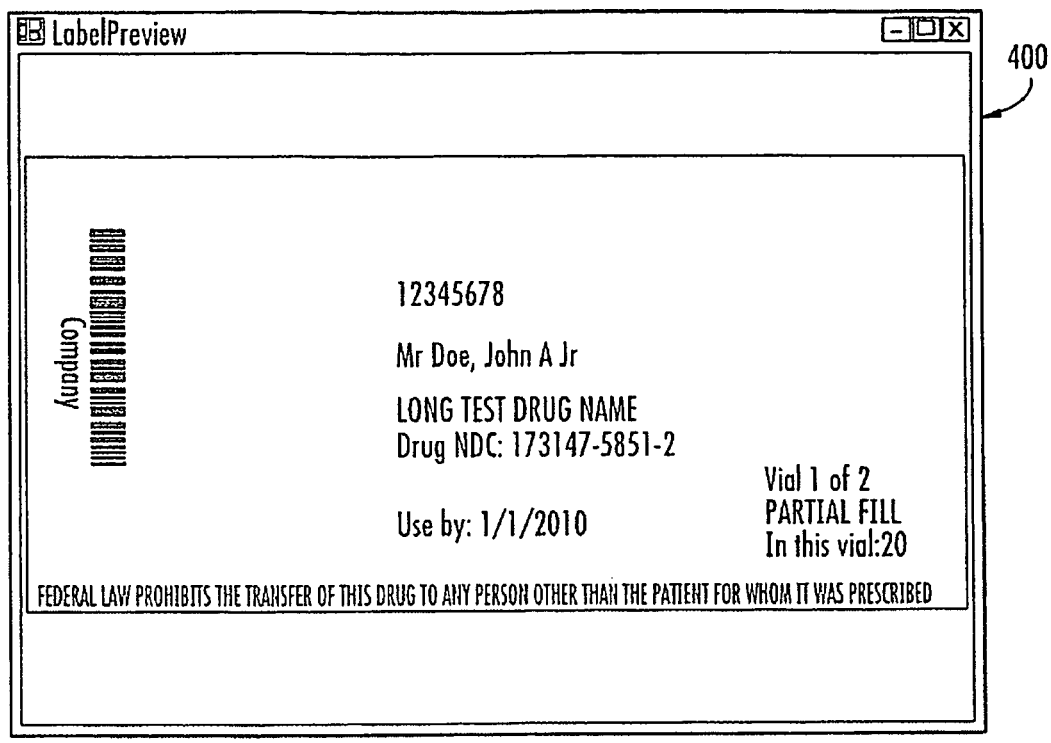

The new data field 131 can be moved to any location within the label template 130 and can be modified to display the text "Partial Fill" in any of various ways. A user can move the new data field 131 by touching the new data field with a finger or stylus and dragging the data field 131 to the desired location. As illustrated in FIG. 23, the user has moved the new data field 131 near the lower right-hand corner of the label template 130. Also, the user has resized the new data field 131, as illustrated. Referring to FIG. 24, a preview of a label produced using the label template 130 of FIG. 23 and containing the new data field 131 is illustrated in preview GUI 400.

Figure 25:
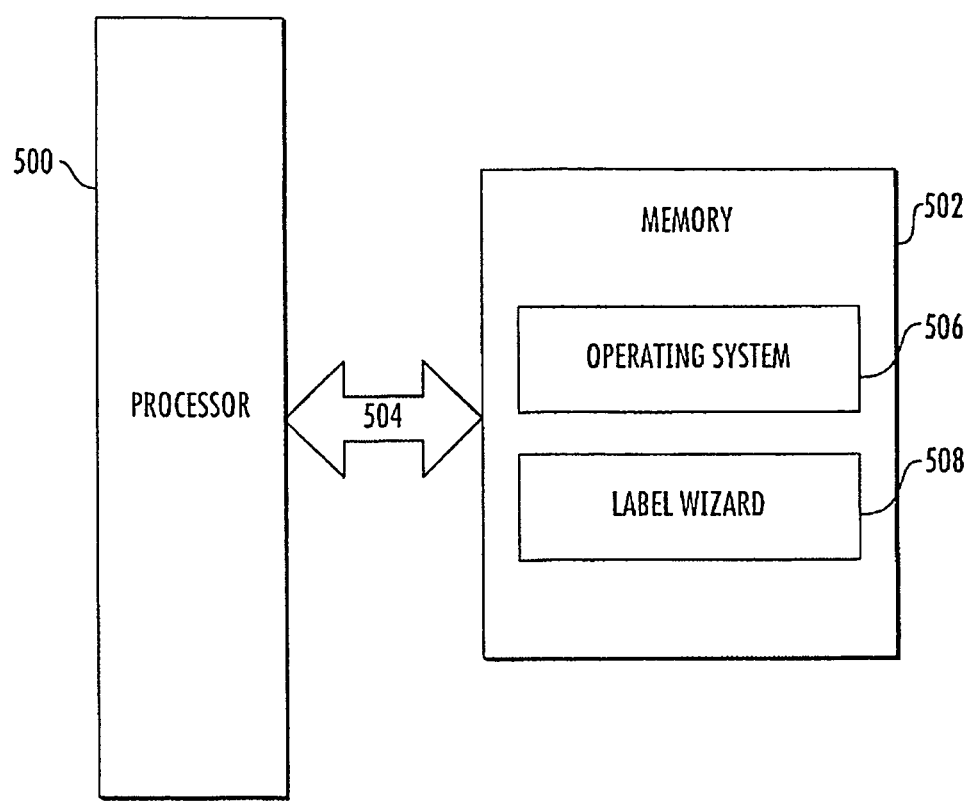
FIG. 25 is a block diagram that illustrates a software architecture for implementing operations of a label wizard, in accordance with some embodiments of the present invention.

FIG. 25 illustrates a processor 500 and a memory 502 that may be used to implement the operations of the label wizard illustrated in FIGS. 4-24, according to some embodiments of the present invention. For example, in some embodiments of the present invention, the processor 500 and memory 502 may be used to embody the processors and the memories used in creating and modifying labels for the pharmaceutical dispensing apparatus 40. The processor 500, memory 502, and data storage may be internally located within a pharmaceutical dispensing apparatus 40 or may be externally located, for example, in another device that communicates with the pharmaceutical dispensing apparatus 40.

The processor 500 communicates with the memory 502 via an address/data bus 504. The processor 500 may be, for example, a commercially available or custom microprocessor. The memory 502 is representative of the overall hierarchy of memory devices containing the software and data used to create and modify labels for a pharmaceutical dispensing apparatus 40. The memory 502 may include, but is not limited to, the following types of devices: cache, ROM, PROM, EPROM, EEPROM, flash, SRAM, and DRAM.

As shown in FIG. 25, the memory 502 may hold two or more major categories of software and data: an operating system 506, and a label wizard module 508. The operating system 506 controls operations of the label wizard module 508. The label wizard module 508 comprises logic for creating and modifying labels as described above with respect to the various GUIs illustrated in FIGS. 4-24.

Although FIG. 25 illustrates an exemplary software architecture that may facilitate creating and modifying labels for a pharmaceutical dispensing apparatus 40, it will be understood that the present invention is not limited to such a configuration, but is intended to encompass any configuration capable of carrying out the operations described herein.

Computer program code for carrying out operations of the label wizard module 508 may be written in a high-level programming language, such as Python, Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

According to some embodiments of the present invention, computer program code for carrying out operations of the label wizard module 508 may be located on a server or other data processing machine directly connected to an automated pharmacy machine. In other embodiments, computer program code for carrying out operations of the label wizard module 508 may be located on a remote data processing device. According to some embodiments, the label wizard is configured to connect to a pharmaceutical dispensing apparatus 40 through sockets, and can load/save data in file form.

In some embodiments, a pharmaceutical dispensing apparatus 40 is capable of reading/saving label files. Accordingly, label data can be exported from a pharmaceutical dispensing apparatus 40 into a file, and sent to a remote location where a label wizard is executing. The label wizard can execute with the received data file, and modify the data. The modified data can be sent back to the pharmaceutical dispensing apparatus 40 for use in printing labels.

Figure 26:
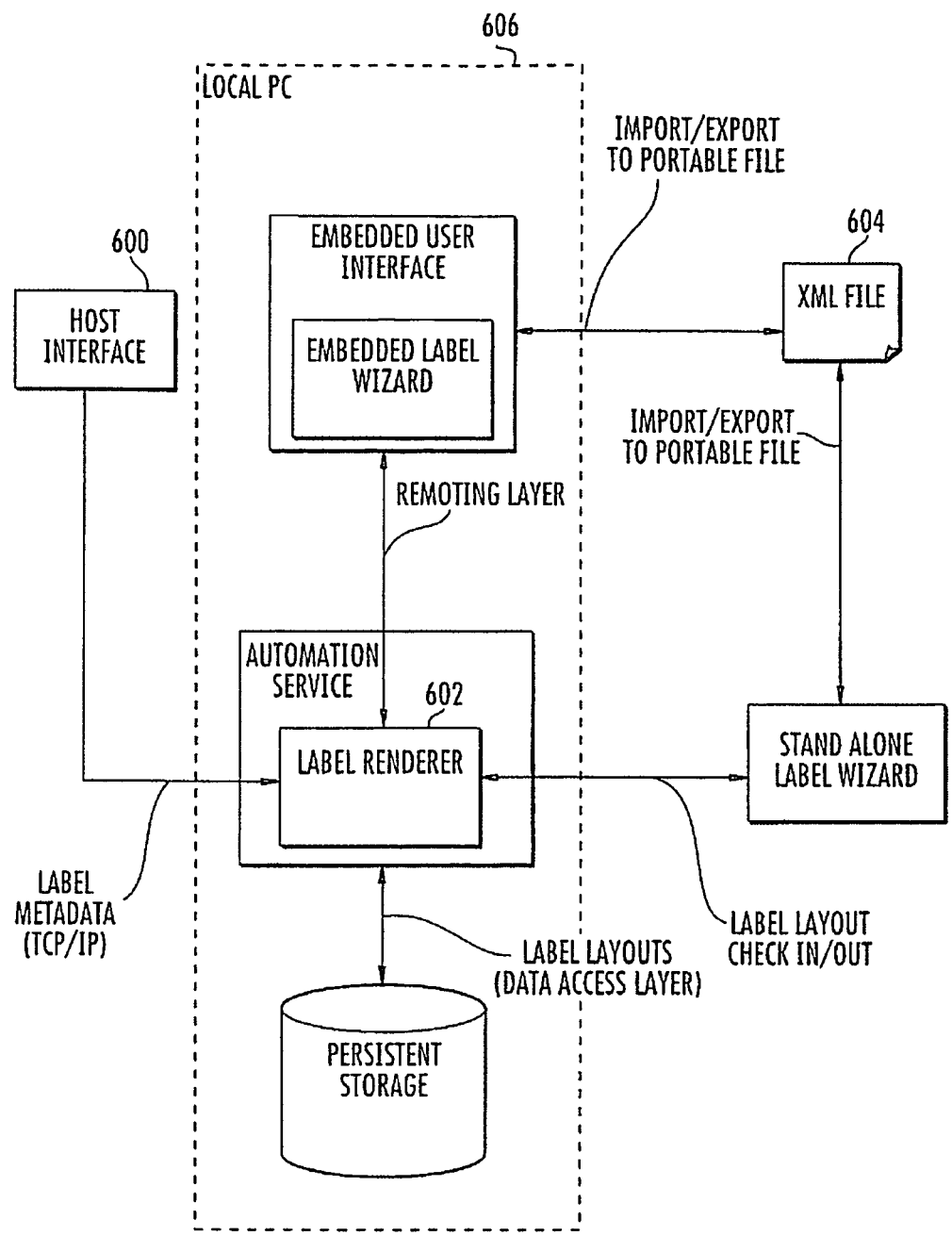
FIGS. 26-27 are block diagrams that illustrate hardware implementations of some embodiments of the present invention.
Figure 27:
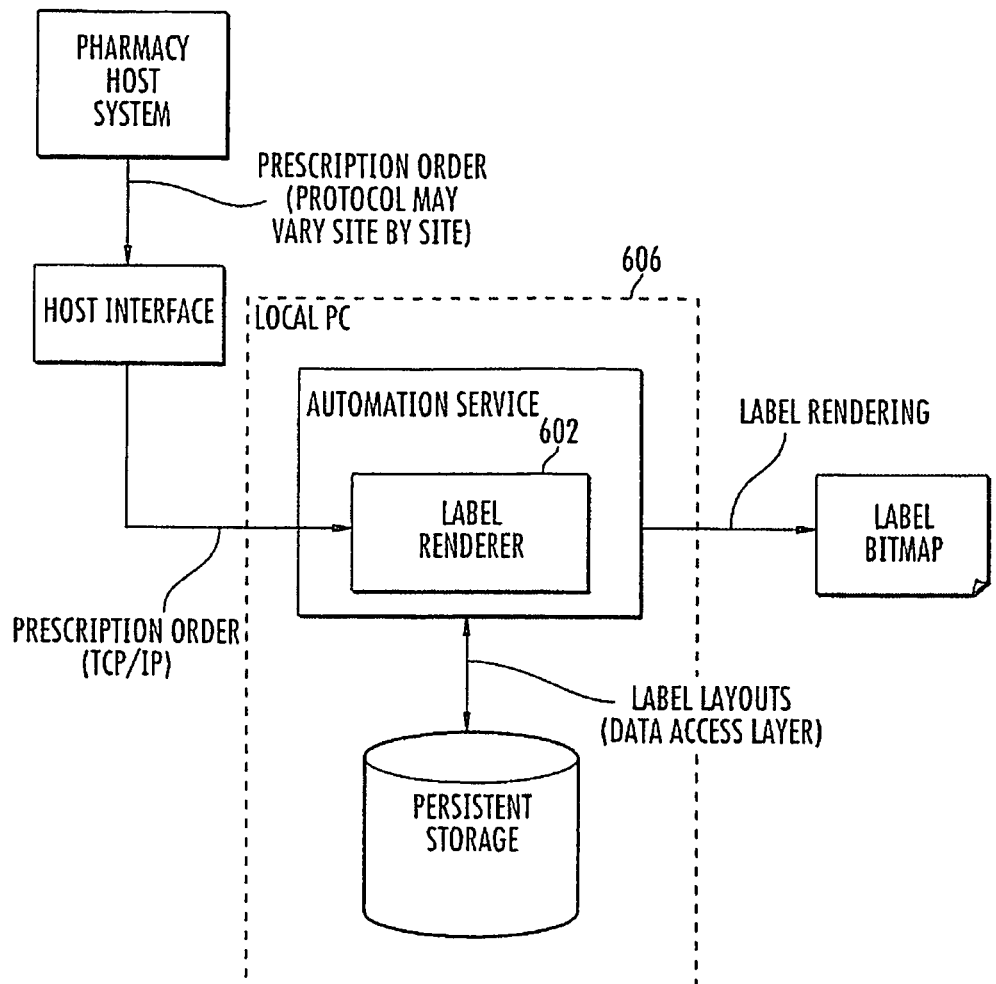

FIGS. 26-27 are block diagrams that illustrate hardware implementations of some embodiments of the present invention. In FIG. 26, the host interface 600 publishes label metadata to the label renderer 602. The embedded label wizard communicates with the label renderer 602 to edit the label layout data. The label layout data can also be exported and imported into an xml file (or other type of file) 604. The stand alone label wizard is an application that may run on a separate PC 606 and can either import the label data from a pharmaceutical dispensing apparatus (e.g., 40, FIGS. 2-3) unit or from a file. Likewise, the edited data can be transmitted back to the pharmaceutical dispensing apparatus or saved to a file for manual import.

In FIG. 27, a label renderer 602 uses the layout configured by the label wizard described above to create a bitmap for a prescription label.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A pharmaceutical dispensing apparatus, comprising:
a touch screen;
a processor;
memory coupled to the processor; and
a computer program residing in the memory that is executable by the processor for guiding a user through a process of creating and modifying a label via the touch screen,
wherein the computer program displays a graphical user interface (GUI) on the touch screen, a label template within the GUI, a display area within the GUI adjacent to the label template that contains a list of selectable data fields that can be used to build a label within the label template, and a toolbox area within the GUI adjacent to the label template that contains a plurality of touch-activated GUI controls adjacent to the template, wherein the GUI controls allow a user to perform one or more of the following functions: change data field size, change data field orientation, and change font type and size of alphanumeric characters displayed within a data field,
wherein the toolbox area further includes a touch-activated GUI control that allows a user to zoom the display of a data field in the template, and
wherein the label template is adapted to receive a plurality of data fields by a user from the display area adjacent to the label template, wherein each data field is adapted to receive and display respective data, wherein at least one data field can be dragged in any direction and to any location within the label template by a user's finger or stylus in direct contact with the at least one data field;
a label printer that prints labels created and modified via the computer program; and
a labeling station that applies printed labels to pharmaceutical vials, wherein the labeling station is positioned to receive a printed label from the label printer.

2. The pharmaceutical dispensing apparatus of claim 1, wherein at least one data field displayed within the label template automatically receives and displays information from data storage in response to display of the at least one data field within the label template.

3. The pharmaceutical dispensing apparatus of claim 1, wherein the computer program includes a label wizard for guiding a user through the process of creating and modifying a label within the label template, wherein the label wizard sequentially displays a plurality of GUIs within the touch screen that guide the user through a process of adding data fields to the label template and entering data within the data fields.

4. The pharmaceutical dispensing apparatus of claim 1, wherein the display area within the GUI further includes a series of label selection tabs positioned above the label template display area that can be utilized to create the following type of labels: manual prescription order label, calibration prescription order labels, cell labels, and dispensing bin labels.

5. The pharmaceutical dispensing apparatus of claim 1, wherein the computer program further displays a touch-activated GUI control adjacent to the template that allows a user to zoom the display of the template within the GUI.

6. The pharmaceutical dispensing apparatus of claim 5, wherein the GUI control that allows a user to zoom the display of the template comprises a slider control positioned adjacent to the label template that is movable by a user's finger or stylus in contact with the touch screen.

7. The pharmaceutical dispensing apparatus of claim 1, wherein the list of selectable data fields comprises one or more of the following: drug name data field, patient name data field, pill quantity data field, barcode data field, drug expiration date data field, prescription order number data field, and drug code data field.

8. A pharmaceutical dispensing apparatus, comprising:
a touch screen;
a processor;
memory coupled to the processor; and
a computer program residing in the memory that is executable by the processor, wherein the computer program includes a label wizard for guiding a user through a process of creating and modifying a prescription label via the touch screen, wherein the computer program displays a graphical user interface (GUI) on the touch screen, a label template within the GUI, a display area within the GUI adjacent to the label template that contains a list of selectable data fields that can be used to build a label within the label template, and a toolbox area within the GUI adjacent to the label template that contains a plurality of touch-activated GUI controls adjacent to the template, wherein the GUI controls allow a user to perform one or more of the following functions: change data field size, change data field orientation, and change font type and size of alphanumeric characters displayed within a data field,
wherein the toolbox area further includes a touch-activated GUI control that allows a user to zoom the display of a data field in the template, wherein the label template is adapted to receive a plurality of data fields by a user from the display area adjacent to the label template, wherein each data field is adapted to receive and display respective data, wherein at least one data field can be dragged in any direction and to any location within the label template by a user's finger or stylus in direct contact with the at least one data field, and wherein the label wizard sequentially displays a plurality of GUIs within the touch screen that guide the user through a process of adding data fields to the label template and entering data within the data fields;

a label printer that prints prescription labels created and modified via the computer program; and a labeling station that applies printed labels to pharmaceutical vials, wherein the labeling station is positioned to receive a printed label from the label printer.

9. The pharmaceutical dispensing apparatus of claim 8, wherein at least one data field displayed within the label template automatically receives and displays information from data storage in response to display of the at least one data field within the label template.

10. The pharmaceutical dispensing apparatus of claim 8, wherein the display area within the GUI further includes a series of label selection tabs positioned above the label template display area that can be utilized to create the following type of labels: manual prescription order label, calibration prescription order labels, cell labels, and dispensing bin labels.

11. The pharmaceutical dispensing apparatus of claim 8, wherein the computer program further displays a touch-activated GUI control adjacent to the template that allows a user to zoom the display of the template within the GUI.

12. The pharmaceutical dispensing apparatus of claim 11, wherein the GUI control that allows a user to zoom the display of the template comprises a slider control positioned adjacent to the label template that is movable by a user's finger or stylus in contact with the touch screen.

13. An apparatus, comprising:
a touch screen;
a processor;
memory coupled to the processor; and
a computer program residing in the memory that is executable by the processor for guiding a user through a process of creating and modifying a prescription label via the touch screen, wherein the computer program displays a graphical user interface (GUI) on the touch screen, a label template within the GUI, a display area within the GUI adjacent to the label template that contains a list of selectable data fields that can be used to build a label within the label template, and a toolbox area within the GUI adjacent to the label template that contains a plurality of touch-activated GUI controls adjacent to the template, wherein the GUI controls allow a user to perform one or more of the following functions: change data field size, change data field orientation, and change font type and size of alphanumeric characters displayed within a data field, wherein the toolbox area further includes a touch-activated GUI control that allows a user to zoom the display of a data field in the template, and wherein the label template is adapted to receive a plurality of data fields inputted by a user therein, wherein each data field is adapted to receive and display respective prescription data, wherein at least one data field can be dragged in any direction and to any location within the label template by a user's finger or stylus in direct contact with the at least one data field;

a label printer that prints prescription labels created and modified via the computer program; and a labeling station that applies printed labels to pharmaceutical vials, wherein the labeling station is positioned to receive a printed label from the label printer.

14. The apparatus of claim 13, wherein at least one data field displayed within the label template automatically receives and displays prescription information from data storage in response to display of the at least one data field within the label template.

15. The apparatus of claim 13, wherein the computer program includes a label wizard for guiding a user through the process of creating and modifying a label within the label template, wherein the label wizard sequentially displays a plurality of GUIs within the touch screen that guide the user through a process of adding data fields to the label template and entering prescription data within the data fields.

16. The pharmaceutical dispensing apparatus of claim 13, wherein the computer program further displays a touch-activated GUI control adjacent to the template that allows a user to zoom the display of the template within the GUI.

17. The pharmaceutical dispensing apparatus of claim 13, wherein the display area within the GUI further includes a series of label selection tabs positioned above the label template display area that can be utilized to create the following type of labels: manual prescription order label, calibration prescription order labels, cell labels, and dispensing bin labels.

* * * * *